United States Patent [19]

Protter et al.

[11] Patent Number: 4,943,527
[45] Date of Patent: Jul. 24, 1990

[54] MATURE APOAI PROTEIN PRODUCTION UNDER SERUM FREE CULTURING CONDITIONS

[75] Inventors: Andrew A. Protter, Palo Alto; Jean-Louis Vigne, San Francisco; Joanne B. Mallory, San Jose; Karen D. Talmadge, Palo Alto; John P. Kane, Hillsborough, all of Calif.

[73] Assignee: California Biotechnology Inc., Mountain View, Calif.

[21] Appl. No.: 834,300

[22] Filed: Feb. 27, 1986

Related U.S. Application Data

[63] Continuation-in-part of Ser. No. 804,692, Dec. 4, 1985, abandoned, which is a continuation-in-part of Ser. No. 784,418, Oct. 4, 1985, abandoned.

[51] Int. Cl.$^5$ .................. C12P 21/05; C12P 21/02; C12N 15/00
[52] U.S. Cl. ...................... 435/69.6; 435/70; 435/172.3; 435/320; 935/11; 935/34; 935/36; 935/60; 935/70
[58] Field of Search ............... 435/68, 172.3, 70, 240, 435/253, 255, 256, 240.1, 240.2, 320; 935/34, 37, 41, 48, 60, 61, 69, 70, 73; 530/359, 412, 415; 536/27; 514/2

[56] References Cited

U.S. PATENT DOCUMENTS

| 4,349,629 | 9/1982 | Carey et al. | 435/68 |
| 4,399,216 | 8/1983 | Axel et al. | 435/68 |
| 4,546,082 | 10/1985 | Kurjan et al. | 435/68 |
| 4,579,821 | 4/1986 | Palmiter et al. | 435/68 |

OTHER PUBLICATIONS

Edelstein et al., *J Biol Chem*, vol. 258, pp. 11430–11434, 1983.
Laub et al., *J Biol Chem*, vol. 258, pp. 6043–6050, 1983.
Fritz et al., *Proc Natl Acad Sci*, vol. 84, pp. 4117–4118, 1986.
Bojunouski et al., *J Lipid Res*, vol. 26, pp. 185–193, 1985.
Breslow et al., *Proc Natl Acad Sci*, 79:6861–6865, Nov., 1982 (USA).
Levene et al., *Acta Paediatrica Scandinavica*, 73:454–460, 1984, (Stockholm, Sweden).
Parks et al., *Journal of Biological Chemistry* 260, No. 5:3155–3163, Mar. 10, 1985 (USA).
McCormick et al., *Molecular and Cellular Biology* 4, No. 1: 166–172, Jan. 1984 (USA).
Karin et al., *Proc Natl Acad Sci* 80: 4040–4044, Jul. 1983 (USA).
Brosius et al., *Proc Natl Acad Sci* 81: 6929–6933, Nov. 1984 (USA).

(List continued on next page.)

*Primary Examiner*—Robin Teskin
*Attorney, Agent, or Firm*—Irell & Manella

[57] ABSTRACT

A method of producing a purified lipid-binding peptide which can bind to phospholipids at one or more amphipatic alpha-helical peptide regions. The method includes providing a gene coding for the peptide, and introducing the gene in expressible, heterologous form in a suitable expression system capable of synthesizing a mixture of peptides which includes the lipid-binding peptide. Addition of either endogenous or exogenous lipids to the peptide mixture forms a low-density lipopeptide complex composed of lipid and the lipid-binding peptide, and this complex can be separated easily from nonlipid-binding peptides in the peptide on the basis of its size and/or density. The method is intended particularly for scaled-up production of purified human apolipoproteins and their alpha-helical lipid-binding regions. Also disclosed are related methods for producing recombinant apolipoproteins, therapeutic lipopeptide compositions, and a stabilized lipid emulsion for nutritional therapy. Further disclosed are methods for expressing apolipoproteins or lipid-binding segments thereof in bacterial, yeast and mammalian cell expression systems, and methods for purifying lipid binding proteins, including fused recombinant proteins.

4 Claims, 27 Drawing Sheets

OTHER PUBLICATIONS

Sharpe et al., *Nucleic Acids Research* 12, No. 9:3917–3932, 1984 (Oxford, England).
Weinberg et al., *Journal Lipid Research:* 24:52–59, 1983 (USA).
Mao et al., *Biochemistry* 16, No. 16: 4150–4156, 1977 (USA).
Jackson et al., *Journal of Biological Chemistry* 250, No. 18:7204–7209, Sep. 25, 1975 (USA).
Weinberg et al., (1985) *J Lipid Res* 26:26.
Weingerg et al., (1985) *J Biol Chem* 260:4919.
Seilhamer et al., (1984) *DNA* 3:309.
Moore et al., (1984) *Biochem Biophys Res Commun* 123:1.
Bogouski et al., (1984) *Proc Natl Acad Sci* (USA) 81:5021.
Knott et al., (1984) *Nucl Acids Res* 12:3909.
Sharpe et al., (1984) *Nucl Acid Res* 12:3917.
Protter et al., (1984) *DNA* 3:449.
Das et al., (1985) *J Biol Chem* 260:6240.

The translated sequence is:

```
                                        29
GCC GCT GAG GAG CCC GCC CAG CCA GCC AGG GCC GCG AGG CCG AGG CCA GGC CGC 83                                110
AGC CCA GGA GCC GCC CCA CCG CAG CTG GCG ATG GAC CCG CCG AGG CCC GCG CTG
                                        MET Asp Pro Pro Arg Pro Ala Leu
                                        ←

137                               164
CTG GCG CTG CTG GCG CTG CCT GCG CTG CTG CTG CTG CTG CTG GCG GGC GCC AGG
Leu Ala Leu Leu Ala Leu Pro Ala Leu Leu Leu Leu Leu Leu Ala Gly Ala Arg
——————————————————————— signal peptide ————————————————————————

191                                    218
GCC GAA GAG GAA ATG CTG GAA AAT GTC AGC CTG GTC TGT CCA AAA GAT GCG ACC
Ala Glu Glu Glu MET Leu Glu Asn Val Ser Leu Val Cys Pro Lys Asp Ala Thr
—→

245                                    272
CGA TTC AAG CAC CTC CGG AAG TAC ACA TAC AAC TAT GAG GCT GAG AGT TCC AGT
Arg Phe Lys His Leu Arg Lys Tyr Thr Tyr Asn Tyr Glu Ala Glu Ser Ser Ser 299                                    326
GGA GTC CCT GGG ACT GCT GAT TCA AGA AGT GCC ACC AGG ATC AAC TGC AAG GTT
Gly Val Pro Gly Thr Ala Asp Ser Arg Ser Ala Thr Arg Ile Asn Cys Lys Val 353                                    380
GAG CTG GAG GTT CCC CAG CTC TGC AGC TTC ATC CTG AAG ACC AGC CAG TGC ATC
Glu Leu Glu Val Pro Gln Leu Cys Ser Phe Ile Leu Lys Thr Ser Gln Cys Ile 407                                    434
CTG AAA GAG GTG TAT GGC TTC AAC CCT GAG GGC AAA GCC TTG CTG AAG AAA ACC
Leu Lys Glu Val Tyr Gly Phe Asn Pro Glu Gly Lys Ala Leu Leu Lys Lys Thr 461                                    488
AAG AAC TCT GAG GAG TTT GCT GCA GCC ATG TCC AGG TAT GAG CTC AAG CTG GCC
Lys Asn Ser Glu Glu Phe Ala Ala Ala MET Ser Arg Tyr Glu Leu Lys Leu Ala 515                                    542
ATT CCA GAA GGG AAG CAG GTT TTC CTT TAC CCG GAG AAA GAT GAA CCT ACT TAC
Ile Pro Glu Gly Lys Gln Val Phe Leu Tyr Pro Glu Lys Asp Glu Pro Thr Tyr
```

```
                                          569                                        596
ATC CTG AAC ATC AAG AGG GGC ATC ATT TCT GCC CTC CTG GTT CCC CCA GAG ACA
Ile Leu Asn Ile Lys Arg Gly Ile Ile Ser Ala Leu Leu Val Pro Pro Glu Thr 623                                        650
GAA GAA GCC AAG CAA GTG TTG TTT CTG GAT ACC GTG TAT GGA AAC TGC TCC ACT
Glu Glu Ala Lys Gln Val Leu Phe Leu Asp Thr Val Tyr Gly Asn Cys Ser Thr 677                                        704
CAC TTT ACC GTC AAG ACG AGG AAG GGC AAT GTG GCA ACA GAA ATA TCC ACT GAA
His Phe Thr Val Lys Thr Arg Lys Gly Asn Val Ala Thr Glu Ile Ser Thr Glu 731                                        758
AGA GAC CTG GGG CAG TGT GAT CGC TTC AAG CCC ATC CGC ACA GGC ATC AGC CCA
Arg Asp Leu Gly Gln Cys Asp Arg Phe Lys Pro Ile Arg Thr Gly Ile Ser Pro 785                                        812
CTT GCT CTC ATC AAA GGC ATG ACC CGC CCC TTG TCA ACT CTG ATC AGC AGC AGC
Leu Ala Leu Ile Lys Gly MET Thr Arg Pro Leu Ser Thr Leu Ile Ser Ser Ser 839                                        866
CAG TCC TGT CAG TAC ACA CTG GAC GCT AAG AGG AAG CAT GTG GCA GAA GCC ATC
Gln Ser Cys Gln Tyr Thr Leu Asp Ala Lys Arg Lys His Val Ala Glu Ala Ile 893                                        920
TGC AAG GAG CAA CAC CTC TTC CTG CCT TTC TCC TAC AAG AAT AAG TAT GGG ATG
Cys Lys Glu Gln His Leu Phe Leu Pro Phe Ser Tyr Lys Asn Lys Tyr Gly MET 947                                        974
GTA GCA CAA GTG ACA CAG ACT TTG AAA CTT GAA GAC ACA CCA AAG ATC AAC AGC
Val Ala Gln Val Thr Gln Thr Leu Lys Leu Glu Asp Thr Pro Lys Ile Asn Ser 1001                                       1028
CGC TTC TTT GGT GAA GGT ACT AAG AAG ATG GGC CTC GCA TTT GAG AGC ACC AAA
Arg Phe Phe Gly Glu Gly Thr Lys Lys MET Gly Leu Ala Phe Glu Ser Thr Lys 1055                                       1082
TCC ACA TCA CCT CCA AAG CAG GCC GAA GCT GTT TTG AAG ACT CTC CAG GAA CTG
Ser Thr Ser Pro Pro Lys Gln Ala Glu Ala Val Leu Lys Thr Leu Gln Glu Leu
```

```
                                  1109                                                1136
AAA AAA CTA ACC ATC TCT GAG CAA AAT ATC CAG AGA GCT AAT CTC TTC AAT AAG
Lys Lys Leu Thr Ile Ser Glu Gln Asn Ile Gln Arg Ala Asn Leu Phe Asn Lys 1163                                                1190
CTG GTT ACT GAG CTG AGA GGC CTC AGT GAT GAA GCA GTC ACA TCT CTC TTG CCA
Leu Val Thr Glu Leu Arg Gly Leu Ser Asp Glu Ala Val Thr Ser Leu Leu Pro 1217                                                1244
CAG CTG ATT GAG GTG TCC AGC CCC ATC ACT TTA CAA GCC TTG GTT CAG TGT GGA
Gln Leu Ile Glu Val Ser Ser Pro Ile Thr Leu Gln Ala Leu Val Gln Cys Gly 1271                                                1298
CAG CCT CAG TGC TCC ACT CAC ATC CTC CAG TGG CTG AAA CGT GTG CAT GCC AAC
Gln Pro Gln Cys Ser Thr His Ile Leu Gln Trp Leu Lys Arg Val His Ala Asn 1325                                                1352
CCC CTT CTG ATA GAT GTG GTC ACC TAC CTG GTG GCC CTG ATC CCC GAG CCC TCA
Pro Leu Leu Ile Asp Val Val Thr Tyr Leu Val Ala Leu Ile Pro Glu Pro Ser 1379                                                1406
GCA CAG CAG CTG CGA GAG ATC TTC AAC ATG GCG AGG GAT CAG CGC AGC CGA GCC
Ala Gln Gln Leu Arg Glu Ile Phe Asn MET Ala Arg Asp Gln Arg Ser Arg Ala 1433                                                1460
ACC TTG TAT GCG CTG AGC CAC GCG GTC AAC AAC TAT CAT AAG ACA AAC CCT ACA
Thr Leu Tyr Ala Leu Ser His Ala Val Asn Asn Tyr His Lys Thr Asn Pro Thr 1487                                                1514
GGG ACC CAG GAG CTG CTG GAC ATT GCT AAT TAC CTG ATG GAA CAG ATT CAA GAT
Gly Thr Gln Glu Leu Leu Asp Ile Ala Asn Tyr Leu MET Glu Gln Ile Gln Asp 1541                                                1568
GAC TGC ACT GGG GAT GAA GAT TAC ACC TAT TTG ATT CTG CGG GTC ATT GGA AAT
Asp Cys Thr Gly Asp Glu Asp Tyr Thr Tyr Leu Ile Leu Arg Val Ile Gly Asn 1595                                                1622
ATG GGC CAA ACC ATG GAG CAG TTA ACT CCA GAA CTC AAG TCT TCA ATC CTG AAA
MET Gly Gln Thr MET Glu Gln Leu Thr Pro Glu Leu Lys Ser Ser Ile Leu Lys
```

```
                                    1649                                              1676
TGT GTC CAA AGT ACA AAG CCA TCA CTG ATG ATC CAG AAA GCT GCC ATC CAG GCT
Cys Val Gln Ser Thr Lys Pro Ser Leu MET Ile Gln Lys Ala Ala Ile Gln Ala 1703                                              1730
CTG CGG AAA ATG GAG CCT AAA GAC AAG GAC CAG GAG GTT CTT CTT CAG ACT TTC
Leu Arg Lys MET Glu Pro Lys Asp Lys Asp Gln Glu Val Leu Leu Gln Thr Phe 1757                                              1784
CTT GAT GAT GCT TCT CCG GGA GAT AAG CGA CTG GCT GCC TAT CTT ATG TTG ATG
Leu Asp Asp Ala Ser Pro Gly Asp Lys Arg Leu Ala Ala Tyr Leu MET Leu MET 1811                                              1838
AGG AGT CCT TCA CAG GCA GAT ATT AAC AAA ATT GTC CAA ATT CTA CCA TGG GAA
Arg Ser Pro Ser Gln Ala Asp Ile Asn Lys Ile Val Gln Ile Leu Pro Trp Glu 1865                                              1892
CAG AAT GAG CAA GTG AAG AAC TTT GTG GCT TCC CAT ATT GCC AAT ATC TTG AAC
Gln Asn Glu Gln Val Lys Asn Phe Val Ala Ser His Ile Ala Asn Ile Leu Asn 1919                                              1946
TCA GAA GAA TTG GAT ATC CAA GAT CTG AAA AAG TTA GTG AAA GAA GCT CTG AAA
Ser Glu Glu Leu Asp Ile Gln Asp Leu Lys Lys Leu Val Lys Glu Ala Leu Lys 1973                                              2000
GAA TCT CAA CTT CCA ACT GTC ATG GAC TTC AGA AAA TTC TCT CGG AAC TAT CAA
Glu Ser Gln Leu Pro Thr Val MET Asp Phe Arg Lys Phe Ser Arg Asn Tyr Gln 2027                                              2054
CTC TAC AAA TCT GTT TCT CTT CCA TCA CTT GAC CCA GCC TCA GCC AAA ATA GAA
Leu Tyr Lys Ser Val Ser Leu Pro Ser Leu Asp Pro Ala Ser Ala Lys Ile Glu 2081                                              2108
GGG AAT CTT ATA TTT GAT CCA AAT AAC TAC CTT CCT AAA GAA AGC ATG CTG AAA
Gly Asn Leu Ile Phe Asp Pro Asn Asn Tyr Leu Pro Lys Glu Ser MET Leu Lys 2135                                              2162
ACT ACC CTC ACT GCC TTT GGA TTT GCT TCA GCT GAC CTC ATC GAG ATT GGC TTG
Thr Thr Leu Thr Ala Phe Gly Phe Ala Ser Ala Asp Leu Ile Glu Ile Gly Leu
```

```
                                                2189                                              2216
GAA GGA AAA GGC TTT GAG CCA ACA TTG GAA GCT CTT TTT GGG AAG CAA GGA TTT
Glu Gly Lys Gly Phe Glu Pro Thr Leu Glu Ala Leu Phe Gly Lys Gln Gly Phe 2243                                              2270
TTC CCA GAC AGT GTC AAC AAA GCT TTG TAC TGG GTT AAT GGT CAA GTT CCT GAT
Phe Pro Asp Ser Val Asn Lys Ala Leu Tyr Trp Val Asn Gly Gln Val Pro Asp 2297                                              2324
GGT GTC TCT AAG GTC TTA GTG GAC CAC TTT GGC TAT ACC AAA GAT GAT AAA CAT
Gly Val Ser Lys Val Leu Val Asp His Phe Gly Tyr Thr Lys Asp Asp Lys His 2351                                              2378
GAG CAG GAT ATG GTA AAT GGA ATA ATG CTC AGT GTT GAG AAG CTG ATT AAA GAT
Glu Gln Asp MET Val Asn Gly Ile MET Leu Ser Val Glu Lys Leu Ile Lys Asp 2405                                              2432
TTG AAA TCC AAA GAA GTC CCG GAA GCC AGA GCC TAC CTC CGG ATC TTG GGA GAG
Leu Lys Ser Lys Glu Val Pro Glu Ala Arg Ala Tyr Leu Arg Ile Leu Gly Glu 2459                                              2486
GAG CTT GGT TTT GCC AGT CTC CAT GAC CTC CAG CTC CTG GGA AAG CTG CTT CTG
Glu Leu Gly Phe Ala Ser Leu His Asp Leu Gln Leu Leu Gly Lys Leu Leu Leu 2513                                              2540
ATG GGT GCC CGC ACT CTG CAG GGG ATC CCC CAG ATG ATT GGA GAG GTC ATC AGG
MET Gly Ala Arg Thr Leu Gln Gly Ile Pro Gln MET Ile Gly Glu Val Ile Arg 2567                                              2594
AAG GGC TCA AAG AAT GAC TTT TTT CTT CAC TAC ATC TTC ATG GAG AAT GCC TTT
Lys Gly Ser Lys Asn Asp Phe Phe Leu His Tyr Ile Phe MET Glu Asn Ala Phe 2621                                              2648
GAA CTC CCC ACT GGA GCT GGA TTA CAG TTG CAA ATA TCT TCA TCT GGA GTC ATT
Glu Leu Pro Thr Gly Ala Gly Leu Gln Leu Gln Ile Ser Ser Ser Gly Val Ile 2675                                              2702
GCT CCC GGA GCC AAG GCT GGA GTA AAA CTG GAA GTA GCC AAC ATG CAG GCT GAA
Ala Pro Gly Ala Lys Ala Gly Val Lys Leu Glu Val Ala Asn MET Gln Ala Glu
```

```
                                         2729                                                        2756
CTG GTG GCA AAA CCC TCC GTG TCT GTG GAG TTT GTG ACA AAT ATG GGC ATC ATC
Leu Val Ala Lys Pro Ser Val Ser Val Glu Phe Val Thr Asn MET Gly Ile Ile 2783                                                        2810
ATT CCG GAC TTC GCT AGG AGT GGG GTC CAG ATG AAC ACC AAC TTC TTC CAC GAG
Ile Pro Asp Phe Ala Arg Ser Gly Val Gln MET Asn Thr Asn Phe Phe His Glu 2837                                                        2864
TCG GGT CTG GAG GCT CAT GTT GCC CTA AAA GCT GGG AAG CTG AAG TTT ATC ATT
Ser Gly Leu Glu Ala His Val Ala Leu Lys Ala Gly Lys Leu Lys Phe Ile Ile 2891                                                        2918
CCT TCC CCA AAG AGA CCA GTC AAG CTG CTC AGT GGA GGC AAC ACC TAT TAC ATT
Pro Ser Pro Lys Arg Pro Val Lys Leu Leu Ser Gly Gly Asn Thr Tyr Tyr Ile 2945                                                        2972
TGG TCT CTA CCA CCA AAA CCG GAG GTG ATC CCA CCT CTC ATT GAG AAC AGG CAG
Trp Ser Leu Pro Pro Lys Pro Glu Val Ile Pro Pro Leu Ile Glu Asn Arg Gln 2999                                                        3026
TCC TGG TCA GTT TGC AAG CAA GTC TTT CCT GGC CTG AAT TAC TGC ACC TCA GGC
Ser Trp Ser Val Cys Lys Gln Val Phe Pro Gly Leu Asn Tyr Cys Thr Ser Gly 3053                                                        3080
GCT TAC TCC AAC GCC AGC TCC ACA GAC TCC GCC TCC TAC TAT CCG CTG ACC GGG
Ala Tyr Ser Asn Ala Ser Ser Thr Asp Ser Ala Ser Tyr Tyr Pro Leu Thr Gly 3107                                                        3134
GAC ACC AGA TTA GAG CTG GAA CTG AGG CCT ACA GGA GAG ATT GAG CAG TAT TCT
Asp Thr Arg Leu Glu Leu Glu Leu Arg Pro Thr Gly Glu Ile Glu Gln Tyr Ser 3161                                                        3188
GTC AGC GCA ACC TAT GAG CTC CAG AGA GAG GAC AGA GCC TTG GTG GAT ACC CTG
Val Ser Ala Thr Tyr Glu Leu Gln Arg Glu Asp Arg Ala Leu Val Asp Thr Leu 3215                                                        3242
AAG TTT GTA ACT CAA GCA GAA GGT GCG AAG CAG ACT GAG GCT ACC ATG ACA TTC
Lys Phe Val Thr Gln Ala Glu Gly Ala Lys Gln Thr Glu Ala Thr MET Thr Phe
```

```
                                    3269                                              3296
AAA TAT AAT CGG CAG AGT ATG ACC TTG TCC AGT GAA GTC CAA ATT CCG GAT TTT
Lys Tyr Asn Arg Gln Ser MET Thr Leu Ser Ser Glu Val Gln Ile Pro Asp Phe 3323                                              3350
GAT GTT GAC CTC GGA ACA ATC CTC AGA GTT AAT GAT GAA TCT ACT GAG GGC AAA
Asp Val Asp Leu Gly Thr Ile Leu Arg Val Asn Asp Glu Ser Thr Glu Gly Lys 3377                                              3404
ACG TCT TAC AGA CTC ACC CTG GAC ATT CAG AAC AAG AAA ATT ACT GAG GTC GCC
Thr Ser Tyr Arg Leu Thr Leu Asp Ile Gln Asn Lys Lys Ile Thr Glu Val Ala 3431                                              3458
CTC ATG GGC CAC CTA AGT TGT GAC ACA AAG GAA GAA AGA AAA ATC AAG GGT GTT
Leu MET Gly His Leu Ser Cys Asp Thr Lys Glu Glu Arg Lys Ile Lys Gly Val 3485                                              3512
ATT TCC ATA CCC CGT TTG CAA GCA GAA GCC AGA AGT GAG ATC CTG CCC ACT GGT
Ile Ser Ile Pro Arg Leu Gln Ala Glu Ala Arg Ser Glu Ile Leu Pro Thr Gly 3539                                              3566
CGC CTG CCA AAC TGC TTC TCA AAT GGA CTC ATC TGC TAC AGC TTA TGG CTC CAC
Arg Leu Pro Asn Cys Phe Ser Asn Gly Leu Ile Cys Tyr Ser Leu Trp Leu His 3593                                              3620
AGT TTC CAA GAG GTG GCA TGG CAT TAT GAT GAA GAG AAG ATT GAA TTT GAA TGG
Ser Phe Gln Glu Val Ala Trp His Tyr Asp Glu Glu Lys Ile Glu Phe Glu Trp 3647                                              3674
AAC AGA GGC ACC AAT GTA GAT ACC AAA AAA ATG ACT TCC AAT TTC CCT GTG GAT
Asn Arg Gly Thr Asn Val Asp Thr Lys Lys MET Thr Ser Asn Phe Pro Val Asp 3701                                              3728
CTC TCC GAT TAT CCT AAG AGC TTG CAT ATG TAT GCT AAT AGA CTC CTG GAT CAC
Leu Ser Asp Tyr Pro Lys Ser Leu His MET Tyr Ala Asn Arg Leu Leu Asp His 3755                                              3782
AGA GTC CCT CAA ACA GAC ATG ACT TTC CGG CAC GTG GGT TCC AAA TTA ATA GTT
Arg Val Pro Gln Thr Asp MET Thr Phe Arg His Val Gly Ser Lys Leu Ile Val
```

```
                                       3809                                                  3836
GCA ATG AGC TCA TGG CTT CAG AAG GCA TCT GGG AGT CTT CCT TAT ACC CAG ACT
Ala MET Ser Ser Trp Leu Gln Lys Ala Ser Gly Ser Leu Pro Tyr Thr Gln Thr 3863                                                  3890
TTG CAA GAC CAC CTC AAT AGC CTG AAG GAG TTC AAC CTC CAG AAC ATG GGA TTG
Leu Gln Asp His Leu Asn Ser Leu Lys Glu Phe Asn Leu Gln Asn MET Gly Leu 3917                                                  3944
CCA GAC TTC CAC ATC CCA GAA AAC CTC TTC TTA AAA AGC GAT GGC CGG GTC AAA
Pro Asp Phe His Ile Pro Glu Asn Leu Phe Leu Lys Ser Asp Gly Arg Val Lys 3971                                                  3998
TAT ACC TTG AAC AAG AAC AGT TTG AAA ATT GAG ATT CCT TTG CCT TTT GGT GGC
Tyr Thr Leu Asn Lys Asn Ser Leu Lys Ile Glu Ile Pro Leu Pro Phe Gly Gly 4025                                                  4052
AAA TCC TCC AGA GAT CTA AAG ATG TTA GAG ACT GTT AGG ACA CCA GCC CTC CAC
Lys Ser Ser Arg Asp Leu Lys MET Leu Glu Thr Val Arg Thr Pro Ala Leu His 4079                                                  4106
TTC AAG TCT GTG GGA TTC CAT CTG CCA TCT CGA GAG TTC CAA GTC CCT ACT TTT
Phe Lys Ser Val Gly Phe His Leu Pro Ser Arg Glu Phe Gln Val Pro Thr Phe 4133                                                  4160
ACC ATT CCC AAG TTG TAT CAA CTG CAA GTG CCT CTC CTG GGT GTT CTA GAC CTC
Thr Ile Pro Lys Leu Tyr Gln Leu Gln Val Pro Leu Leu Gly Val Leu Asp Leu 4187                                                  4214
TCC ACG AAT GTC TAC AGC AAC TTG TAC AAC TGG TCC GGC CTC CTA CAG TGG TGG
Ser Thr Asn Val Tyr Ser Asn Leu Tyr Asn Trp Ser Gly Leu Leu Gln Trp Trp 4241                                                  4268
CAA CAC CAG CAC AGA CCA TTT CAG CTT CGG GCT CGT TAC CAC ATG AAG GCT GAC
Gln His Gln His Arg Pro Phe Gln Leu Arg Ala Arg Tyr His MET Lys Ala Asp 4295                                                  4322
TCT GTG GTT GAC CTG CTT TCC TAC AAT GTG CAA GGA TCT GGA GAA ACA ACA TAT
Ser Val Val Asp Leu Leu Ser Tyr Asn Val Gln Gly Ser Gly Glu Thr Thr Tyr
```

```
                                                 4349                                                      4376
GAC CAC AAG AAT ACG TTC ACA CTA TCA TGT GAT GGG TCT CTA CGC CAC AAA TTT
Asp His Lys Asn Thr Phe Thr Leu Ser Cys Asp Gly Ser Leu Arg His Lys Phe 4403                                                      4430
CTA GAT TCG AAT ATC AAA TTC AGT CAT GTA GAA AAA CTT GGA ATC AAC CCA GTC
Leu Asp Ser Asn Ile Lys Phe Ser His Val Glu Lys Leu Gly Ile Asn Pro Val 4457                                                      4484
TCA AAA GGT TTA CTA ATA TTC GAT GCA TCT AGT TCC TGG GGA CCA CAG ATG TCT
Ser Lys Gly Leu Leu Ile Phe Asp Ala Ser Ser Ser Trp Gly Pro Gln MET Ser 4511                                                      4538
GCT TCA GTT CAT TTG GAC TCC AAA AAG AAA CAG CAT TTG TTT GTC AAA GAA GTC
Ala Ser Val His Leu Asp Ser Lys Lys Lys Gln His Leu Phe Val Lys Glu Val 4565                                                      4592
AAG ATT GAT GGG CAG TTC AGA GTC TCT TCG TTC TAT GCT AAA GGC ACA TAT GGC
Lys Ile Asp Gly Gln Phe Arg Val Ser Ser Phe Tyr Ala Lys Gly Thr Tyr Gly 4619                                                      4646
CTG TCT TGT CAG AGG GAT CCT AAC ACT GGC CGG CTC AAT GGA GAG TCC AAC CTG
Leu Ser Cys Gln Arg Asp Pro Asn Thr Gly Arg Leu Asn Gly Glu Ser Asn Leu 4673                                                      4700
AGG TTT AAC TCC TCC TAC CTC CAA GGC ACC AAC CAG ATA ACT GAA AGA TAT GAA
Arg Phe Asn Ser Ser Tyr Leu Gln Gly Thr Asn Gln Ile Thr Glu Arg Tyr Glu 4727                                                      4754
GAT GGA ACC CTC TCC CTC ACC TCC ACC TCT GAT CTG CAA AGT GGC ATC ATT AAA
Asp Gly Thr Leu Ser Leu Thr Ser Thr Ser Asp Leu Gln Ser Gly Ile Ile Lys 4781                                                      4808
AAT ACT GCT TCC CTA AAG TAT GAG AAC TAC GAG CTG ACT TTA AAA TCT GAC ACC
Asn Thr Ala Ser Leu Lys Tyr Glu Asn Tyr Glu Leu Thr Leu Lys Ser Asp Thr 4835                                                      4862
AAT GGG AAG TAT AAG AAC TTT GCC ACT TCT AAC AAG ATG GAT ATG ACC TTC TCT
Asn Gly Lys Tyr Lys Asn Phe Ala Thr Ser Asn Lys MET Asp MET Thr Phe Ser
```

FIG. 18-9

```
                                        4889                                              4916
AAG CAA AAT GCA CTG CTG CGT TCT GAA TAT CAG GCT GAT TAC GAG TCA TTG AGG
Lys Gln Asn Ala Leu Leu Arg Ser Glu Tyr Gln Ala Asp Tyr Glu Ser Leu Arg 4943                                              4970
TTC TTC AGC CTG CTT TCT GGA TCA CTA AAT TCC CAT GGT CTT GAG TTA AAT GCT
Phe Phe Ser Leu Leu Ser Gly Ser Leu Asn Ser His Gly Leu Glu Leu Asn Ala 4997                                              5024
GAC ATC TTA GGC ACT GAC AAA ATT AAT AGT GGT GCT CAC AAG GCG ACA CTA AGG
Asp Ile Leu Gly Thr Asp Lys Ile Asn Ser Gly Ala His Lys Ala Thr Leu Arg 5051                                              5078
ATT GGC CAA GAT GGA ATA TCT ACC AGT GCA ACG ACC AAC TTG AAG TGT AGT CTC
Ile Gly Gln Asp Gly Ile Ser Thr Ser Ala Thr Thr Asn Leu Lys Cys Ser Leu

5105
CTG GTG CTG GAG AAT GAT G
Leu Val Leu Gly Asn Asp Ala
```

FIG. 18-10

MATURE APOAI PROTEIN PRODUCTION UNDER SERUM FREE CULTURING CONDITIONS

CROSS-REFERENCE TO RELATED APPLICATION

This application is a continuation-in-part of U.S. patent application Ser. No. 804,692, filed Dec. 4, 1985, now abandoned which is a continuation-in-part of U.S. patent application Ser. No. 784,418, filed Oct. 4, 1985 now abandoned.

1. Field of the Invention

The present invention relates to lipid-binding peptides, methods of producing, purifying and formulating the peptides, and novel lipopeptide compositions.

2. Background of the Invention

Lipid-binding proteins and their peptide fragments are potentially important in a number of therapeutic applications. One major class of lipoproteins are the serum lipoproteins which are present in a variety of macromolecular protein/lipid complexes which transport and regulate serum levels of cholesterol, triglycerides, phospholipids, and other serum lipids. Since many cardiovascular diseases are related to lipid imbalances, it has been proposed to treat such diseases by administering one or more apolipoproteins or apolipoprotein/lipid complexes which can exert a counter effect on an undesired pattern of lipid accumulation in the tissues of the patient.

Apolipoproteins share a common design with respect to the arrangement of lipid-binding regions. In general terms, the proteins have a segment or segments which contain a series of amphipatic α-helical lipid binding regions. Some of the proteins also have a relatively polar region which may be a receptor-binding region or play some other protein-identification role.

For some of the proposed therapeutic applications, the apolipoprotein is designed to perform a protein-specific function involving the more polar region. Applications of this type are expected to require the polar regions of the complete mature apolipoproteins. In other applications—and particularly those involving lipid-binding function only, it is likely that a number of different apolipoproteins, or the lipid-binding segments thereof, could function interchangeably.

In order to bring such therapeutic application of lipoproteins to a practical stage, it is necessary to produce the lipid-binding proteins in high-levels and usually, in relatively pure form. Although the apolipoproteins may be isolated from human serum, the purification schemes are time consuming, and the yields of some are relatively poor. In particular, difficulties arise in attempting to separate selected apolipoprotein types from one another. These difficulties are illustrated by current methods for purifying serum apolipoprotein A-4 (Weinberg, L. B. et al, J Lipid Res 26:26 (1985); and Weinberg, R. B., et al, J Biol Chem 260:4914 (1985)). Also, proteins purified by these methods can be contaminated with infectious viruses, such as hepatitis.

Recombinant DNA expression represents an alternative approach which potentially can overcome some of the limitations inherent in isolation of serum proteins. Several groups, including the inventors, have reported genomic and cDNA sequences for a number of different apolipoproteins, including apolipoprotein AI (abbreviated apoAI) (Seilhamer, J. J., et al, DNA 3:309 (1984)), apoAII (Moore, et al, Biochem Biophys Res Commun 123:1 (1984), apoAIV (Bogouski, D., et al, Proc Natl Acad Sci (U.S.A.) 81:5021 (1984)), apoCI (Knott, et al, Nucl Acids Res 12:3909 (1984), apoCII (Sharpe, C. R., et al, Nuc Acid Res 12:3917 (1984)), apoCIII (Protter, A. H., et al, DNA 3:180 (1984)), and apoE (Das, H. K., et al, J Biol Chem 260:6240 (1985)). Heretofore, however, no group has successfully achieved expression of a recombinant apolipoprotein or lipid-binding segment thereof.

Even if successful expression of apolipoproteins is achieved, it will be necessary, for practical applications, to produce the protein efficiently and at high levels on a large-scale basis. Also it will be important to provide a method for purifying large quantities of the protein by a simple and efficient method.

3. Summary of the Invention

It is therefore a general object of the present invention to provide a method for producing apolipoproteins for their lipid-binding segments in purified form, in a system which is readily adaptable to large-scale production.

A related object of the invention is to provide a high-producing expression system capable of producing and secreting recombinant apolipoprotein in processed, or mature, form.

Another related object of the invention is to provide a method for use in an expression system in which a heterologous lipid-binding peptide is present in a mixture of proteins produced by the system, for separating the lipid-binding peptide by simple floatation and/or size-related fractionation procedures.

Yet another object of the invention is to provide a stabilized nutritional emulsion which can be formulated in large scale using methods of the invention.

Producing a nascent high-density lipoprotein complex by simple recombinant DNA methods is still another object of the invention.

The invention includes a method for producing a purified lipid-binding peptide which can bind to phospholipids at one or more amphipatic alpha-helical peptide regions. In practicing the method, a gene coding for the peptide is introduced in expressible, heterologous form in a suitable expression system capable of synthesizing a mixture of peptides which includes the lipid-binding peptide. Addition of either endogenous or exogenous lipids to the peptide mixture forms a particulate lipopeptide complex composed of lipid and the lipid-binding peptide, and this complex can be separated easily from nonlipid-binding peptides in the peptide mixture on the basis of its size or, preferably, its density.

In one embodiment, the expression system includes Chinese hamster ovary (CHO) cells, and the gene is introduced in an expression vector having a regulatable promoter derived from the human metallothionein II gene. Synthesis of the lipid-binding protein in the system is under the control of the promoter, which is responsive to the concentration of divalent metals in the cell medium. The cells are effective to produce the apolipoprotein in mature, secreted form, and can also form, from endogenous lipid, the lipoprotein complexes which can be readily separated from nonlipid-binding proteins according to the method of the invention. High-producer CHO cells can be selected by clonal selection.

The lipid which is added to the mixture of proteins produced in the expression system may be endogenous lipid, as in CHO cells, or exogenous lipid in the form of emulsion particles or phospholipid vesicles. Interaction of recombinant apolipoproteins or their lipid-binding segments with oil emulsion particles produces an emulsion which is stabilized against particle fusion, or creaming, in certain patients where inflammation is involved, and thus solves an important problem in nutritional lipid-emulsion therapy. Addition of phospholipid vesicles to the apolipoproteins, and particularly apoAI, leads to the formation of disc-like lipoprotein structures which resemble high-density lipoproteins, and which are thus expected to have therapeutic properties in reverse cholesterol transport.

These and other objects and features of the present invention will become more fully apparent when the following detailed description of the invention is read in conjunction with the accompanying drawings.

BRIEF DESCRIPTION OF THE DRAWINGS

FIG. 18–1, 18–10 shows the DNA sequence of the cDNA insert containing the signal sequence and first 1,643 amino acid codons of mature apoB and the corresponding amino acid sequence.

DETAILED DESCRIPTION OF THE INVENTION

Figure 1:
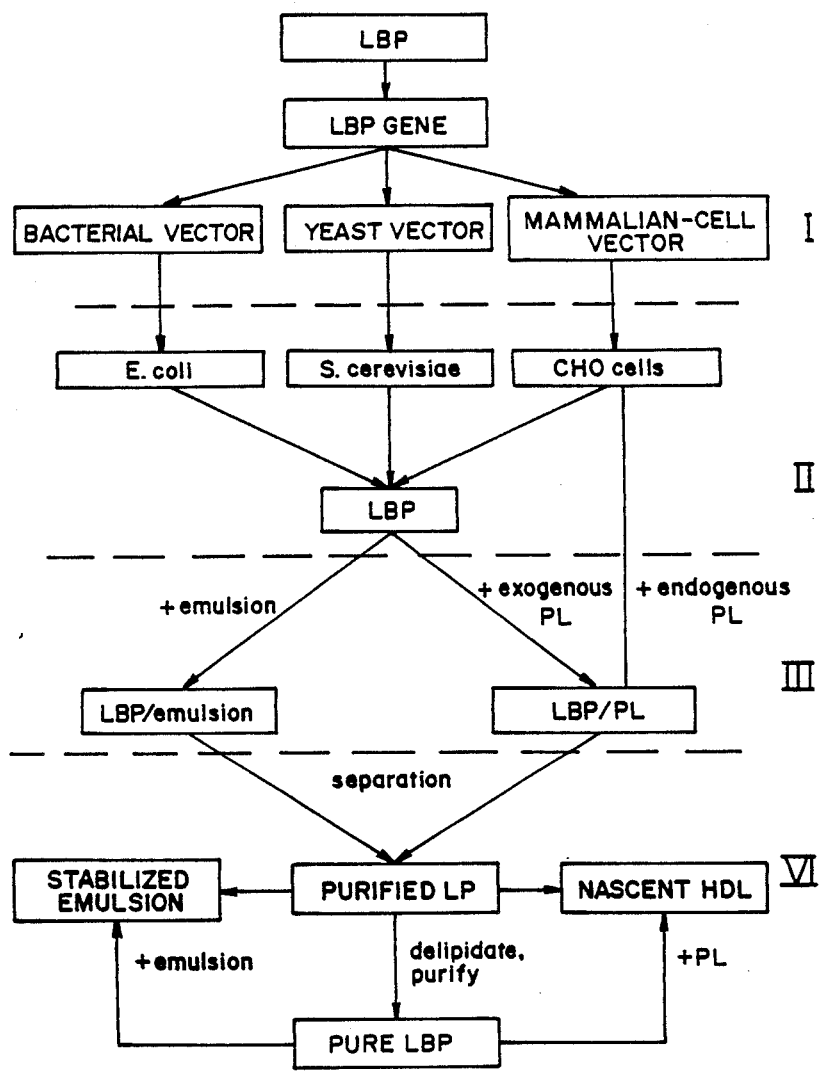
FIG. 1 is a flow diagram showing peptide synthesis, separation, purification, and formulation processes involved in the invention.

FIG. 1 illustrates the general schema of the invention, including processes for expressing, separating, purifying, and formulating lipid-binding peptides (LBP). The upper portion of the flow diagram indicates the steps of (1) selecting of a suitable lipid-binding peptide, (2) constructing or isolating a gene coding for the peptide, and (3) placing the gene in an expression vector. As indicated in the figure, the expression vector may be one designed for use in either a bacterial, yeast, or mammalian-cell expression system. These aspects of the invention are discussed in Section I below. In Section II, methods of expressing the selected LPB in a variety of hosts are described.

The recombinantly produced LBP can be combined with lipids to produce lipid-protein complexes which may take the form of protein-associated triglyceride emulsions (LBP/emulsions) or LBP/phospholipid vesicle/(LBP/PL). Lipid emulsions or phospholipid vesicles may be added exogenously to the LBP, to form the lipoproteins. It has also been discovered, according to one aspect of the invention, that a mammalian-cell expression system, such as Chinese hamster ovary (CHO) cells, can supply endogenous lipids which combine with the expressed LBP to form the desired lipoprotein. These aspects of the invention are considered in Section III. According to another aspect of the invention, the lipoprotein complexes can be separated readily from nonlipid binding proteins on the basis of increased size or density, to yield lipoproteins which are largely purified from nonlipid binding proteins also produced in the expression system. The lipoprotein separation provides a simple, rapid method for purifying lipid-binding peptides such as apolipoproteins in large scale. This approach will be detailed in Section IV.

The purified lipoprotein formed by LBP in association with lipid emulsion may be suitable, without further purification, as a stabilized lipid emulsion for nutritional purposes. Alternatively, the LBP in the emulsion may be further purified and recombined with emulsion lipids to form an emulsion which is generally suitable for parenteral use. The increased stability of the lipoprotein emulsion is discussed in Section V. Similarly, the lipoprotein formed by association with phospholipids is useful directly as a nascent high-density lipoprotein (HDL), or the protein may be further purified and reassociated with phospholipid to form a nascent HDL composition. The utility of nascent HDL in reverse cholesterol uptake is also considered in Section V.

I. LBP Expression Vectors

As defined herein, lipid-binding peptide (LBP) refers to a protein or protein segment which has, or in the presence of phospholipids assumes, an amphipatic alpha-helical structure characterized by a polar side or face that can interact with the polar head groups of phospholipids, and a nonpolar side which can interact with lipid acyl chain groups. The polar face contains charged amino acid residues, typically with acidic groups toward the center of the helix paired with basic residues at the edge, and it has been postulated that these charge pairs are able to form favorable ionic interactions with zwitterionic phospholipid head groups.

The nonpolar face contains largely hydrophobic residues. Compositional and sequence features of alpha-helical lipid-binding peptides are reviewed in Segrest, J. P., et al, FEBS LETT 38:247 (1974).

Human apolipoproteins are one general source of lipid-binding peptides. Apolipoproteins refer to the delipidated proteins which, when combined with lipids, such as triglycerides, cholesterol, cholesterol esters, and phospholipids (Breslow, J. L., Ann Rev Biochem 54:699 (1984)), form various types of lipoprotein complexes. Alpha-helical, amphipatic lipid-binding regions are common to all human apolipoproteins, including apoAI, apoAII, apoAIV, apoB, apoCI, apoCII, apoCIII, apoD, and apoE. The lipid-binding peptide may include the entire apolipoprotein, or one or more lipid-binding regions thereof. The amino acid sequence and composition of the LBP may precisely match that of an apolipoprotein or lipid-binding region(s), or it may contain one or more amino acid substitutions which do not interfere with the LBP's ability to form an alpha-helical structure necessary for lipid binding (neutral substitutions).

The gene coding for selected LBP peptide is defined herein to include any natural or synthetic DNA sequence which codes for the selected LBP, and can be expressed in heterologous form in a suitable expression system. The gene coding for the selected LBP may be derived either from genomic DNA or cDNA (copied from an isolated mRNA). The gene is said to be derived from genomic or cDNA if it includes a partial or full-length DNA sequence coding for: (a) a human apolipoprotein, (b) one or more alpha-helical binding regions thereof, or (c) proteins or peptides containing neutral substitutions in (a) or (b). The gene may also be a synthetic polynucleotide. In the latter case, the coding sequence in the gene is constructed to correspond to the LBP amino acid sequence, or more preferably, to match the known gene sequence of a selected apolipoprotein lipid-binding region, as reported, for example, in the references given above on the full-length cDNA and/or genomic sequence of a variety of apolipoproteins and in Example XVIII. The oligonucleotide can be synthesized, typically as a series of overlapping segments, by known methods.

A partial or full-length genomic DNA or cDNA for a selected apolipoprotein can be obtained according to published methods or by known cloning and selection procedures. The procedures described by the inventors (Seilhamer, J. J, et al, DNA 3:309 (1984)) for obtaining both full-length cDNA and a genomic gene fragment which includes the entire coding region of apoAI are generally applicable. In the published method, a poly A RNA (mRNA) fraction was copied, made double stranded, methylated, and cloned into a λ cloning vector by addition of convenient EcoRI (RI) linkers to the double-strand cDNA ends.

The cDNA inserts were subcloned into a bacterial plasmid, and the resulting plasmid library screened with a 15-mer representing the anti-codons for the last five amino acids of apoAI. One of the clones, containing a 300 bp insert encompassing the 3'-terminal end of apoAI mRNA was selected, and from this an AluI fragment was obtained for use as a probe in screening for full-length cDNA. The largest cDNA probe identified contained a 5' untranslated region 39 nucleotides long, and an open reading frame of 801 nucleotides coding for the complete 267 amino acid prepro-apoAI. Following the TGA termination codon was a 3' untranslated region of 55 nucleotides containing the polyadenylation signal AATAAA and a short polyA tail.

A complete-sequence genomic apoAI gene was obtained by screening the cloned genomic fragment with the above AluI cDNA probe. One 2.2 kb PstI fragment was identified as containing the entire apoAI gene, including 5' and 3' untranslated regions. A comparison of the genomic and cDNA sequences revealed the presence in the genomic gene of three introns which interrupt the coding sequence in (a) the 5' untranslated region, (b) an 18 amino acid signal sequence, and (c) the region coding for the mature peptide.

Example XI describes similar methods for obtaining a full-length genomic clone coding for apoAII. References noted above also give details for obtaining genomic and/or cDNA genes for apo AIV, CII, CIII, and E. Example XVIII describes similar methods for obtaining a cDNA that encodes the signal sequence and first 430 amino acids of apoB, which includes the receptor-binding domain and two amphipatic helices. This cDNA is described in detail in pending co-owned patent application for "Novel Lipoprotein-Based Drug-Delivery Systems", Ser. No. 783,787, filed Oct. 3, 1985.

The LBP gene from above is placed into a suitable expression vector for expression in a bacterial, yeast, or mammalian-cell system. Typically, the vector used in the construction contains the necessary control elements for gene transcription and translation in a selected host system, and one or more restrictions sites at which the heterologous gene can be inserted in expressible form.

Vectors suitable for expressing protein in bacteria, typically E. coli, and yeast, typically S. cerevisiae, are available, and methods for introducing genes in expressible forms into the vectors are known. The Methods section below outlines general procedure for inserting heterologous gene sequences into expression vectors, selecting successful recombinants, and verifying the constructions. The methods described in Example I for construction of a bacterial vector having an apoAI genomic fragment insert, and in Examples III and V, for construction of a bacterial vector and yeast vector, respectively, with a full-length apoAI cDNA insert are generally applicable. Full-length cDNA was used in the vectors designed for production of complete apolipoproteins, to avoid limitations in bacterial and yeast systems in transcribing intron-containing genomic genes. The gene in the yeast vector contained codons for the mature apoAI minus the first seven N-terminal codons.

A preferred mammalian-cell expression vector has been described in co-owned patent application for "A Superior Mammalian Expression System", Ser. No. 701,296, filed Feb. 13, 1985. The vector contains the human metallothionein-II (hMT-II) promoter and is designed to transform Chinese hamster ovary (CHO) cells. The vector/cell system is capable of high levels of expression of the heterologous gene, and gene expression is inducible, under the control of the hMT-II promoter, by addition of divalent metals, such as divalent zinc and iron. Studies performed in support of the present application and other co-owned applications indicate that genomic (intron-containing) genes, and cDNA copies thereof, encoding a variety of protein and protein segments, including apolipoproteins and apolipoprotein α-helical segments, are expressed efficiently and at high levels in the CHO system. As will be seen below, and according to an important feature of the system, the CHO cells are also capable of processing expressed apolipoproteins to mature proteins, and of forming nascent lipoprotein complexes with endogenous producing lipid.

The vector construction methods detailed below for construction of a hMT-II vector containing a full-length genomic apoAI gene (Example VII) and a full-length genomic apoAII gene (Example XII), are generally applicable to other apoproteins and lipid-binding segments thereof. An exemplary CHO expression vector containing the hMT-II promoter and a full-length genomic apoAI coding region under the control of the promoter in a high-producing CHO cell line was deposited with the American Type Culture Collection ATCC Patent Depository on Oct. 3, 1985 and has deposit # CRL 8911. The vector in the deposited CHO cells can be readily manipulated, by known techniques, to substitute other apolipoprotein or protein fragment coding regions for the apoAI region.

In another embodiment of the invention, a gene coding for an LBP is joined to the gene of a second protein or peptide in the expression vector, to produce a fused-protein gene composed of the LBP gene and the coding sequence for a second, typically hydrophilic, protein. The LBP moiety in the expressed fused protein can be used to facilitate protein purification, particularly in a scaled-up production method, according to procedures detailed in Section IV below.

Methods for fusing an LBP gene to a second coding sequence would follow known cloning procedures. Preferably, the LBP gene would be attached at the C-terminus of the second-protein's coding region. If neither peptide moiety contains a methionine residue, the two genes can be fused at a methionine codon, to allow the fused protein to be cleaved into its unfused components, after purification, by cyanogen bromide cleavage, according to known methods.

II. LBP Expression

Expression of the selected LBP gene is achieved by transforming a suitable bacterial, yeast, or mammalian-cell host with the expression vector constructed as above. Methods for transforming bacterial and yeast cells with suitable expression vectors are known, and generally follow the methods outlined in Examples II and IV, for transforming *E. coli*, and Example VI, for transforming *S. cerevisiae*. Also described in these examples are typical reaction conditions under which protein synthesis in the expression system takes place.

To confirm that the expression system has indeed expressed the heterologous LBP, the proteins produced in the system are analyzed for the presence of a peptide that can be distinguished on the basis of its unique size or reactivity with anti-LBP-antibody. For proteins formed in a bacterial expression system, which are often produced as intracellular forms, the cells must be ruptured or lysed, such as by detergent treatment, and the cell debris removed, such as by centrifugation or filtration. The released cellular proteins, when fractionated by sodium dodecyl sulfate polyacrylamide gel electrophoresis (SDS-PAGE), show a series of fractionated proteins which migrate on the gel according to their molecular weight. Comparison of the fractionated proteins from cells transformed either with the LBP-gene vector, or a control vector may show the presence in the LBP cell proteins of a unique molecular weight species corresponding to the expected molecular weight of the LBP. The identity of the LBP can be further confirmed by precipitating the protein mixture with anti-LBP antibody, and fractionating the precipitated material by SDS-PAGE, as described generally in Example II.

Using the above protein identification methods, it is shown in Examples II and IV that a bacterial system (*E. coli*) is capable of producing both a apoAI fragment containing three amphipatic, alpha-helical protein regions and full-sequence apoAI itself. As noted above, the apolipoproteins have strong sequence similarities in their alpha-helical binding regions. The finding herein that the bacterial system is capable of expressing both apoAI and a lipid-binding region thereof indicates that the system is capable of expressing genes which encode apolipoprotein alpha-helical lipid binding regions generally, whether the lipid binding regions are portions of an apolipoprotein, or the full-length apolipoprotein. It is noted that the bacterial system of Examples II and IV does not carry out post-translation processing of the expressed LBP because the gene was tailored to exclude the N-terminus signal sequence and propeptide condon(s).

Similar methods were used to show that a yeast system (*S. cerevisiae*) is capable of expressing apoAI (Example VI). In the yeast system, the LBP are secreted into the extracellular medium, and therefore can be harvested simply by removing cells, such as by centrifugation, from the cell medium.

A preferred system for expression of LBP is the mammalian-cell system composed of CHO cells transformed with the hMT-II promoter vector. For a variety of reasons, this system is well suited to scaled-up production and purification of apolipoproteins and other LBPs. One advantage of the system is its inducibility for LBP expression, by addition of divalent metals to the cell medium. Example X below demonstrates the increasing levels of apoAI production which are produced at increasingly greater zinc concentrations.

Expression levels may be increased substantially in clonal strains of CHO cells which are selected for high production of LBP. Example IX illustrates the selection of clonal variants of the CHO cells which are high producers of mature apoAI. The selection procedure involves culturing the cells under low cell concentration conditions which lead to individual-cell (clonal) colonies in the culture. These colonies are picked and screened for high levels of LBP expression, for example, by dot-blot Western blotting (Jahn et al, Proc Natl Acad Sci (U.S.A.) 81:1684-1687 (1984)). In the selection procedure described in Example IX, about 200 clonal cell colonies were screened. Of these, two high-producing strains produced apoAI at a level about 30 times that of the original CHO cells as a whole. In the high-producer cells, the proportion of apoAI in the secreted protein mixture is between about 30-50%. This high percentage of specific expression contributes, in part, to the ability to obtain substantially purified LBP by a simple lipoprotein separation step (Section IV).

LBP production by the CHO cells can be readily scaled up by culturing the cells in large-volume roller bottles, as described in Example XIX. The CHO strain used here was a high-producing strain, and liquid volume in each bottle was 250 ml. As seen in Table I of the example, apoAI levels of up to 30 mg/liter/day can be achieved.

According to another advantage of the CHO cell system, the apolipoproteins are processed and secreted in mature form. Cellular processing of full-length (pre-pro) apoAI involves cleavage of an 18 amino acid leader sequence, to form the proapoAI, and further cleavage of 6 amino N-terminal residues to form the mature protein. Although earlier studies reported in the above-cited patent application for "A Superior Mammalian Expression System" showed that the system effectively secretes proteins containing a leader sequence, with cleavage of the sequence, it was not known heretofore that the system could further process proapolipoproteins to produce mature proteins. Studies confirming the processing of apoAI to mature protein are detailed in Example XV.

It is known that both apoAI and apoAII have preproapo, proapo, and mature apo forms, and that in the body apparently at least a portion of the processing from the proapo to mature apo form occurs in the serum (Bojanovski, D., et al, J Lipid Res 26:185 (1985)). This suggests that the serum contains special peptidases capable of cleaving the small N-terminal pro peptide from proapo proteins. The finding that the CHO system is capable of processing the proapo form to mature apo form is therefore especially surprising, since the CHO cells are cultured in serum free medium. Apparently the CHO cells contain their own enzyme for carrying out this final processing step. The general procedures for expressing other apolipoproteins in the CHO system have been verified for expression and secretion of apoAII (Example XIX).

III. Forming Lipoprotein Complexes

The bacterial, yeast, and mammalian-cell expression systems described above produce a mixture of proteins (peptides) which include a relatively small proportion of the desired heterologous LBP. For bacterial systems—where the heterologous LBP is not secreted—the LBP-containing mixture is in the intracellular protein fraction and produced by lysing the cells, and removing cellular debris. For yeast and mammalian-cell systems, where the LBP is secreted, the protein mixture is in the extracellular protein fraction remaining after removing the cells from the reaction medium. The number of heterogeneous sized proteins contained in the protein mixtures from the various expression systems can be seen from the SDS gel electrophoretic patterns of expressed proteins in FIGS. 3 and 5 (for *E. coli*), FIG. 7 (for *S. cerevisiae*) and FIGS. 9, 10, and 11 (for CHO cells). Typically the heterologously produced LBP constitutes only about 0.5 to 2 percent of the total protein mixture. In the most favorable system—clonal high-producer CHO cells under favorable metal ion induction conditions—approximately 30–50% of the protein is the desired LBP.

According to one aspect of the invention, the heterologous LBP gene product produced in an expression system can be purified conveniently and in large volume from the protein mixture by (a) adding lipid to the mixture, to form particulate lipoprotein complexes composed of lipid particles and associated LBP, and (b) separating the complex from nonlipid binding peptides in the mixture on the basis of the lower density or greater size of the complex. The present section examines methods for forming such lipoprotein complexes in mixtures of peptides.

The lipid added to an LBP-containing protein mixture may be an oil emulsion, and typically a triglyceride oil emulsion containing a phospholipid emulsifier. Such emulsions are commercially available for use in parenteral nutrition or may be prepared by emulsifying oil/-phospholipid mixtures by homogenization or sonication, according to known procedures. One standard oil emulsion is INTRALIPID, a commercially available triglyceride/phosphatidylcholine emulsion used for parenteral nutrition. The emulsion typically has particle sizes in the 0.1 to 0.5 micron range.

To form the LBP/emulsion complex, the lipid emulsion is added to the LBP-containing protein mixture, and the suspension allowed to incubate for up to one or more hours with shaking. The protein mixture is preferably concentrated to about 5–10 mg/ml before addition of lipids. Lipid is added in a weight ratio of at least about 10:1 lipid/protein and preferably at a ratio of 50:1 or more.

In a second general method, the added lipid is phospholipid, usually taking the form of an aqueous suspension of uni- or multilamellar bilayer structures commonly known as liposomes. Methods for preparing liposome suspensions from phospholipid or phospholipid/cholesterol mixtures are well known. A preferred liposome composition includes phosphatidylchloline (PC), such as egg PC, or a PC/cholesterol mixture. Typically the vesicle forming lipids are dried to a thin film, and hydrated slowly with an aqueous medium, forming a suspension of lipids. The suspension can be further processed, for example, by homogenization or sonication, to reduce the size heterogeneity of the particles. Example XVI below describes the preparation of a PC liposome suspension whose uni- and multilamellar structures are seen in the negative stain photomicrograph of FIG. 16. Liposome particle sizes typically range from about 0.01 to 0.1 microns.

Addition of the lipid suspension to the protein mixture from the expression system, and incubation of the protein/lipid suspension are substantially the same as for lipid emulsion addition to the protein mixture. That is, the liposome suspension is added at a weight ratio of preferably about 10:1 or more, and incubated for up to one or more hours. The morphology of the lipoprotein (LBP/phospholipid) complexes which form will depend on the nature of the apolipoprotein. Where the apolipoprotein is apoAI, the lipoprotein complexes include many disc-like structures, such as those shown in the photomicrograph of FIG. 17. These structure strongly resemble the disc-like nascent high-density lipoprotein (HDL) particles found in liver perfusate and composed predominantly of phospholipid and apoAI and apoE.

As indicated in FIG. 1, a third lipid source is endogenous lipids which are supplied by the expression system itself. Heretofore, it has not been realized that an expression system can supply lipid in an amount and form that is useful in producing particulate lipoprotein complexes with heterologous expressed lipid-binding proteins. The lipids supplied by the system, in the case of CHO cells, are presumably phospholipids which can combine with the expressed LBP to form characteristic LBP/phospholipid structures. A comparison of the photomicrographs of FIGS. 13 and 17 indicates that the lipoprotein particles formed in the CHO system reported in Example XIII, involving apoAI expression, resemble the disc-like structures seen when purified apoAI is mixed with PC liposomes.

IV. Lipoprotein Purification

The particulate lipoprotein complex from above can be separated readily from nonlipid binding proteins in the expression system on the basis of either size or density.

As discussed in Section III, the LBP/lipid complex is a particulate complex composed of lipid particles—either emulsion, liposomal, or lipid-disc particles—with associated LBP. The lipoprotein particles are in the general size range of between about 0.01 to 0.55μ, and as such, can be readily separated from smaller, soluble proteins by particle exclusion in molecular sieve chromatography. The molecular-sieve material is preferably selected to exclude material in the range 500,000 daltons or greater, insuring that essentially all of noncomplexed proteins will be included (retarded) by passage through the chromatography column bed. The larger lipoprotein complex, which is excluded, will elute in the void volume of the column. The eluted fractions can be monitored, conventionally, by UV spectroscopy or the like. Preferred molecular-sieve material includes Agarose 10%, whose exclusion size is about 1,000,000 daltons.

Figure 15:
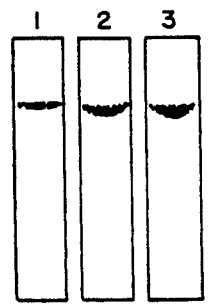
FIG. 15 shows the gel electrophoretic pattern of mature human apoAI produced by roller bottle culture and purified in accordance with the invention.

For large-scale separation, the lipoprotein complex is preferably separated from nonlipid binding peptides by flotation. Typically this is done by adjusting the density of the peptide-mixture medium to between about 1.06–1.21 by addition of a mono- or disaccharide, such as sucrose, or a salt, such as KCl. The medium is then placed in a centrifuge tube, overlayered with a lower density medium, and centrifuged until the complex has concentrated at the top of the tube. The lipoprotein material removed from the gradient may be resuspended in the same density medium and separated a second time, to further remove nonlipid-binding proteins. This procedure is illustrated in Example XIV for the purification of apoAI. As seen in FIG. 15, and discussed in Example XIV, the purification method produced about a 95% purification of apoAI, as judged by a gel density scan of the fractionated protein.

Alternatively, the lipoprotein complex will separate on its own by floatation if allowed to stand undisturbed in a medium of sufficient density. This floatation procedure is, of course, advantageous in large-scale preparation, since both chromatography and centrifugation steps are eliminated.

The LBP associated with the separated lipoprotein complex may be further purified, as necessary, by delipidating the complex and purifying the peptide by conventional purification methods, such as described in Example XV.

The purification method just described is part of a general LBP-producing system in which recombinantly produced LBP is associated to particulate lipid and isolated from nonbinding lipids by simple floatation or molecular sizing procedures. The method is more broadly applicable to purifying other proteins which have lipid-binding regions that promote protein association with particulate lipids. Such proteins include lung surfactant protein, C-reactive protein, and fused LBP proteins of the type described above. In the more general method, particulate lipid is added to a mixture of proteins produced in the expression system, to produce lipid-particle complexes with the heterologous lipophilic protein. The particulate lipoprotein complexes are then separated on the basis of size or density as described.

V. Utility of Lipoprotein Compositions

A. Nascent HDL Composition

It is known that the apoprotein components of the high-density lipoproteins (HDL)—apoAI, apoAII, apoCI, apoCII, and apoCIII—when reconstituted with phospholipid and then incubated in the presence of tissue culture cells, remove cholesterol from the cell membrane in vitro (Jackson, et al, J Biol Chem 250:7204 (1975)) and in vivo (Miller, N. E., et al, Nature 314:109 (1985)). The complex formed by apoAI and phospholipid appears to be particularly effective in reverse cholesterol transport.

As described in Section III, the lipoprotein complex formed by recombinant apoAI and PC liposomes resembles the disc-like structures of nascent HDL. This finding indicates that apolipoproteins formed in accordance with the invention retain their lipid-binding properties and that lipoproteins formed with the recombinant proteins would therefore have the same therapeutic uses, for reverse cholesterol transport, as HDL particles or nascent HDL particles formed with isolated serum apolipoproteins.

B. Other Therapeutic Uses

It is known that either apoAI or apoCI activate lecithin cholesterol acyl transferase (LCAT) in vitro (Soutaw, A. K., et al, Biochem 14:3057 (1975)). LCAT acetylates cholesterol and this is thought to be the mechanism that prevents cholesterol exchange out of HDL. Thus, infusion of apoAI or apoCI or a mixture of both in various lipopeptide mixtures could be effective to enhance LCAT activity and thereby lower the rate of, or prevent, plaque formation and consequent atherosclerotic disease. ApoCII is known to enhance lipoprotein lipase activity in vitro (Shelburne, F. et al, J Clin Invest 65:652 (1980)) which promotes the metabolism of triglyceride-carrying chylomicrons, lowering the serum levels of triglycerides. In fact, deficiency of apoCII has been shown to cause one form of hypertriglyceridemia (Breckenridge, W. C., et al, New Engl J Med 298:1265 (1978)) and apoCII therapy may be effective in controlling this disease. ApoCII and apoCIII are both known to facilitate the removal of triglycerides in vivo (Erkelens, D. W., et al, Metabolism 34:222 (1985)) and they could be important in therapy to lower serum triglyceride levels for the prevention of hypertiglyceridemia. ApoE have been associated with type III lipoproteinemia, (Zannis, V. I. et al, J Biol Chem 255:1759 (1980)). Supplying these patients with the normal protein could be a useful treatment for this disease. ApoB deficiency has been associated with a-β-lipoproteinemia (Barson, F. A. et al, Blood 5:301 (1959)), and preparations with this apolipoprotein could be useful in treating these patients.

C. Stabilized Emulsion

Although fat emulsions are widely used for parenteral nutritional therapy, in many acutely ill patients and in infants, problems relating to instability of emulsion particle size have been encountered. In infants, particle size instability is evidenced by fat accumulation in the lungs, leading to fat embolism and death (Barson, et al, Archives of Disease in Childhood 53:218 (1978)). A similar problem has been observed in acutely ill adults, and it has been shown that the sera of acutely ill patients agglutinate, or cream, lipid emulsions such as INTRALIPID. The conditions most commonly associated with creaming are neoplasia; severe infections, e.g., pneumonia, septicaemia; major surgery; trauma; myocardial infarction and cerebrovascular accident; inflammatory disorders including rheumatoid arthritis; Crohn's disease and polyarteritis nodosa; and lymphoma. This finding has led to the suggestion that C-reactive protein, synthesized at high levels in people stressed by inflammation, tissue injury, or infection (this group includes premature infants), may be enhancing the fusion of INTRALIPID lipid particles to particles of a larger size that are filtered out of the bloodstream by the lungs, sometimes leading to fat embolism and death.

Studies conducted in support of the present invention, and reported in Example XVII show that serum from stressed animals causes a significant size increase in a major portion of INTRALIPID particles, whereas emulsion particle size is substantially stable in serum from unstressed animals (Table IV).

According to an important discovery herein, it was found that the lipoprotein complex formed between apoAI and INTRALIPID is stable in size when exposed to serum from either stressed or unstressed animals. That is, apoAI stabilized the emulsion particles against fusion and size growth in the presence of serum factor(s) (presumably including C-reactive protein) associated with stress.

The invention thus includes a stabilized lipid emulsion for parenteral nutritional use, composed of lipid emulsion particles and associated recombinant apolipoprotein, such as apoAI.

From the foregoing it can be appreciated how various objects and features of the invention are met. The invention provides a method for producing recombinant apolipoproteins, and lipid-binding peptides thereof, in a variety of expression systems, including E. coli, S. cerevisiae, and CHO cells. These recombinant apolipoproteins retain their native lipid-binding properties, as judged both by (a) their ability to bind to added lipid, either in the form of an oil/phospholipid emulsion or phospholipid vesicle suspension, (b) their ability to associate with and stabilize oil/phospholipid emulsion particles against fusion in the presence of fusogenic serum factor(s) and (c) their ability to interact with phospholipid vesicles, producing disc-like structures similar in appearance to nascent HDL particles.

The CHO cell expression system described herein in particular provides several advantages for large-scale production of apolipoproteins and their peptide fragments. The system is inducible for heterologous gene expression, and high-producer clonal strains which are selected readily can increase heterologous gene expression by more than an order of magnitude and to a level in which the recombinant LBP constitutes 30%-50% of total secreted protein. This cell system also has the ability to process full-sequence apolipoproteins to mature proteins, an ability that may require two separate peptide cleavages for apoAI and apoAII.

The lipid-binding capacity of the recombinant proteins is exploited in a simple, efficient method for producing purified apolipoprotein by recombinant methods. The purity of the purified AI may be as high as 95% using only centrifugation steps. The method is especially useful for producing apolipoproteins in large scale, in combination with the high-level CHO expression system.

In broader scope the method of producing pure or nearly pure recombinant protein by lipid addition to recombinantly produced proteins is applicable to any lipid-binding recombinant protein which can associate stably with lipid particles.

Methods

A. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499 (1980).

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5-10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or exonuclease Bal-31 results in hydrolysis of any single-stranded portion.

Ligations are performed in 15-50 µl volumes under the following standard conditions and temperatures: 20 mM Tris-HCl pH 7.5, 10 mM $MgCl_2$, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations (usually employing a 10-30 fold molar excess of linkers) are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{+2}$ using about 1 unit of BAP or CIP per µg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments. The desired sequences are thus recovered from colonies responding to probe.

B. Verification of Construction

In the constructions set forth below, correct ligations for plasmid construction are confirmed by first transforming E. coli strain MC1061 obtained from Dr. M.

Casadaban (Casadaban, M., et al, J Mol Biol 138:179 (1980)) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, Proc Natl Acad Sci (U.S.A.) 62:1159 (1969), optionally following chloramphenicol amplification (Clewell, D. B., J Bacteriol 110:667 (1972)). The isolated DNA is analyzed by restriction and/or sequenced by the dideoxy method of Sanger, F., et al, Proc Natl Acad Sci (U.S.A.) 74:5463 (1977) as further described by Messing, et al, Nucleic Acids Res 9:309 (1981), or by the method of Maxam, et al, Methods in Enzymology 65:499 (1980).

EXAMPLE I

Bacterial Vectors with AI Genomic Fragment

Figure 2A:
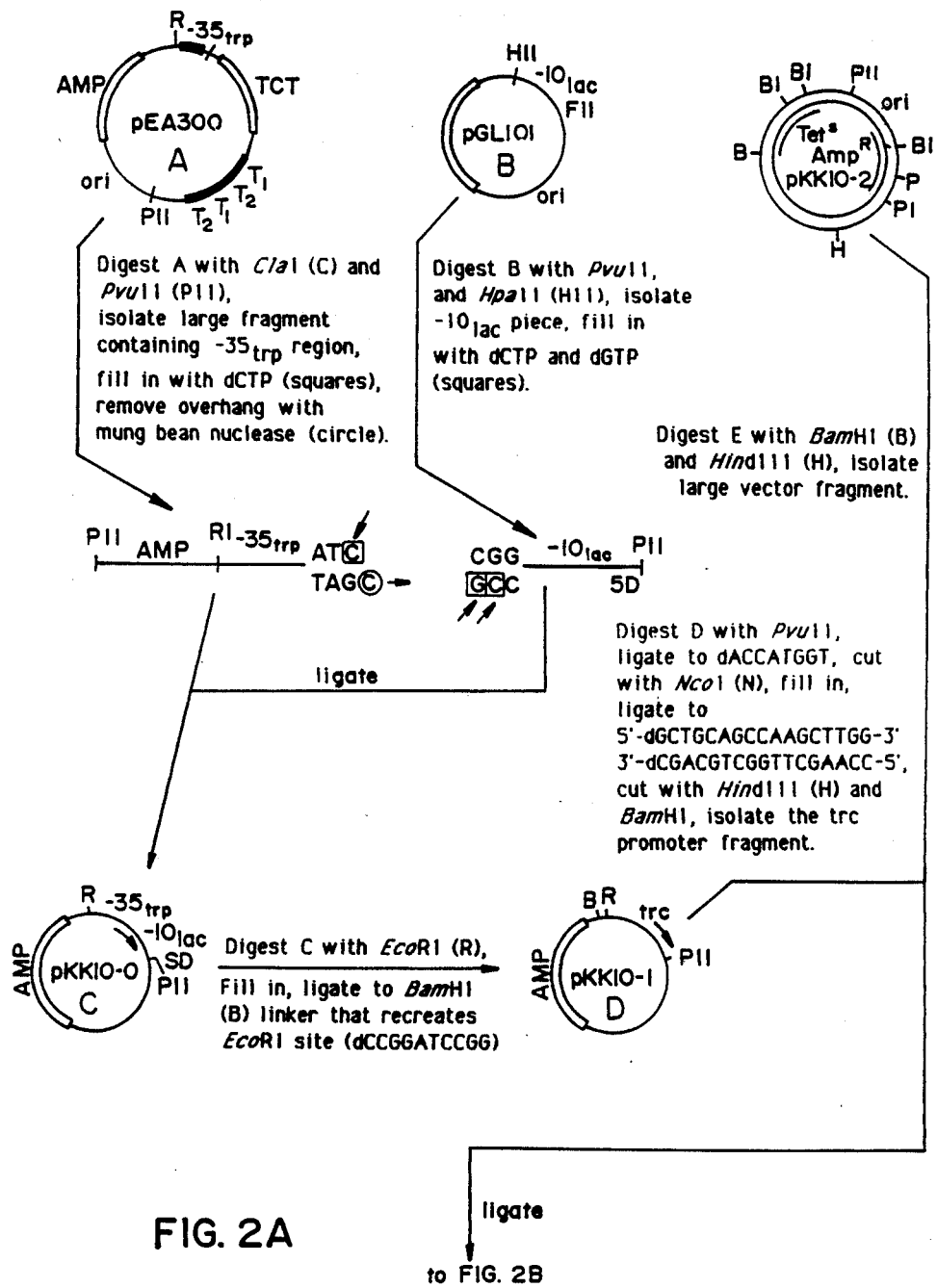
FIG. 2 shows the construction of two bacterial vectors, designated pAp85 and pApoF, designed for expression of human apoAI C-terminal genomic fragment in *E. coli;*
Figure 2B:
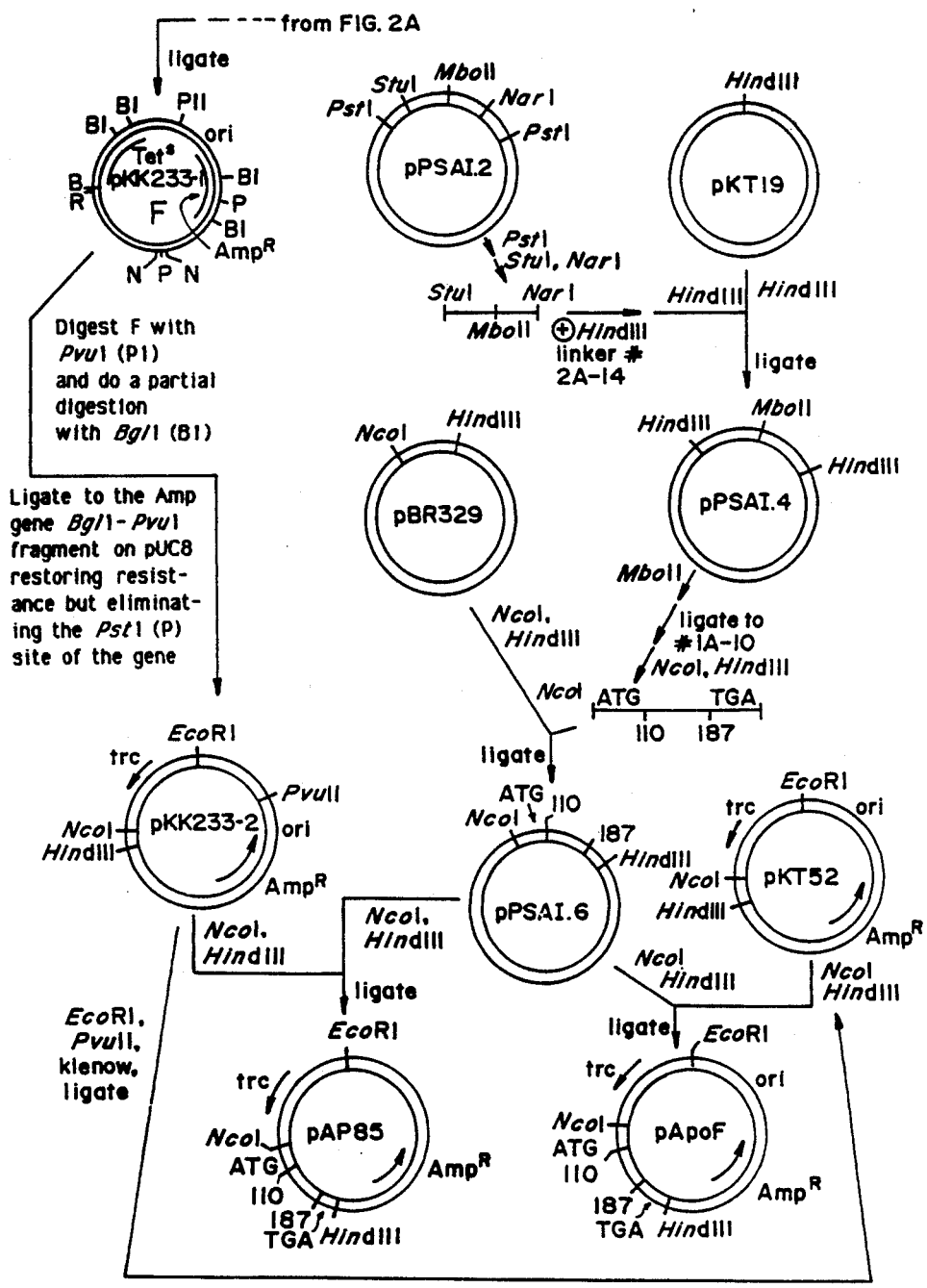

The recombinant phage, λAI-12, containing a 2.2 kb PstI fragment that encodes most of the apoAI gene, including all of the coding sequence, has been described (see Seilhamer, J. J., et al, DNA 3:309 (1984)). Plasmid pPSAI.2 was constructed by isolating the 2.2 kb PstI fragment and inserting it into the PstI site of pBR322 (Maniatis, T., et al, Molecular Cloning: A Laboratory Manual, Cold Spring Harbor Laboratory, NY (1982)). The pPSAI.2 insert was removed by PstI digestion and isolated by gel electrophoresis. The isolated insert (10 μg) was digested with 5 units of StuI, and the 1065 base pair StuI fragment, which includes the part of the apoAI gene region that encodes amino acids 110-187 was isolated and digested with NarI, as shown in FIG. 2. The 5' overhang resulting from NarI digestion was blunt-ended by incubating the DNA with the Klenow fragment of DNA polymerase I in K. L. Buffer (10 mM Tris-HCl, pH 8.0, 5 mM MgCl$_2$), and 0.8 mM each dATP, dTTP, dCTP, and dGTP for 5 hours at 17° C. The self-complementary oligonucleotide #2A-14 (5'-dCCTGAAGCTTCAGG) which contains translation stop signal (TGA) and HindIII site (AAGCTT) was ligated to both ends of the blunt-ended fragment by incubating with 50 units T4 DNA ligase in K. L. Buffer with 10 mM ATP for 12 hours at 12° C. The linkers were cut back with HindIII and the fragment was subcloned into the HindIII site of pKT19 (Talmadge, K., et al, Gene 12:235 (1980)) to give the plasmid pPSAI.4 (FIG. 2).

The pPSAI.4 plasmid (10 μg) was cut with 2 units of MboII for 2 hours at 37° C., and the resulting 3' overhang was removed by treatment with T4 DNA polymerase (Maniatis, et al, supra). The self-complementary oligonucleotide #1A-10 (CATGGCCATG) which contains a translation initiation signal (TGA) was ligated to the MboII cut, blunt-ended DNA fragments, cut with NcoI and HindIII and ligated into pBR329 (catalogued in the National Institutes of Health, Bethesda, MD data base of vectors and gene sequences) which had been cut with NcoI and HindIII (see FIG. 2). The ligation mixtures were used to transform E. coli HB101 cells as described above. Plasmids with the correct insert were identified by restriction mapping. The resulting plasmid, pPSAI.6, includes an NcoI/HindIII fragment with the apoAI gene fragment encoding amino acids 110-187 in frame with an ATG translation initiation signal at the 5' end and a TGA translation stop signal at the 3' end. The NcoI/HindIII insert of pPSAI.6 was isolated and ligated into (a) the expression vector pKK233-2 (Brosius, J., et al, Proc Natl Acad Sci (U.S.A.) 81:6929 (1984)) which had been cut with NcoI and HindIII, and (b) the expression vector pKT52, which had been cut with the same enzymes. pKK233-2 and pKT52 were constructed as follows. The construction of these vectors is described in U.S. Ser. Nos. 616,488 and 622,639, assigned to the same assignee, and incorporated herein by reference. With reference to FIG. 2, the "trc" promoter contains the upstream portions of the trp promoter and the downstream, operator-containing, regions of the lac promoter and was originally prepared from two readily available plasmids containing these promoters. To construct the trc promoter as a BamHI/HindIII cassette, an intermediate plasmid pKK10-0 was prepared containing the hybrid promoter.

To prepare pKK10-0, pEA300 (Amman, E., et al, Gene (1983) 25:167-178) was digested with PvuII and ClaI, filled in using dCTP only in the presence of DNA polymerase (Klenow), followed by digestion with mungbean nuclease, and the large vector fragment isolated. This vector fragment contains the upstream portions of the trp promoter. The fragment was ligated with a 55 bp blunt-ended HpaII/PvuII digest excised from pGL101 (Lauer, G., et al, J Mol Appl Genet (1981) 1:139-147), which was prepared by digesting pGL101 with PvuII and HpaII followed by repair in the presence of dGTP and labeled dCTP. This fragment contains the lac operator region. The ligation product of these two blunt-end fragments was pKK10-0.

A BamHI site was inserted into pKK10-0 upstream of the trp/lac (trc) promoter/operator by digestion with EcoRI, filling in with Klenow, and insertion of the BamHI linker 5'-CCGGATCCGG-3'. The resulting plasmid, pKK10-1 was digested with PvuII, and ligated to the NcoI linker, 5'-ACCATGGT-3', digested with NcoI, filled in, and then ligated to a double-stranded linker containing PstI and HindIII sites provided as two complementary oligonucleotides, 5'-GCTGCAGC-CAAGCTTGG-3' and its complement. The ligation mixture was used to transform E. coli to Amp ®. The isolated plasmid DNA was digested with BamHI and HindIII, and the small BamHI/HindIII fragment obtained on electrophoresis contains the trc promoter.

To complete pKT52, the BamHI/HindIII fragment containing the trc promoter was ligated into the large fragment obtained from BamHI/HindIII digestion of pKK10-2 (Brosius, J., Gene (1984) 27:161-172) which contains the Amp ® gene and the origin of replication. The resulting plasmid, pKK233-1 was digested to completion with PvuI and then partially with BglI and ligated with the 360 bp PvuI/BglI fragment containing the corresponding portion of the ampicillin resistance gene but lacking a PstI site from pUC8. The ligation mixture was used to transform E. coli and transformants were screened for the presence of only one PstI site next to the trc promoter. The correct construction, pKK233-2, was digested with EcoRI and PvuII, filled in with dATP and dTTP, and religated to obtain the correct construction pKT52.

pKT52 contains the desired trc promoter, a downstream ATG start codon, and downstream NcoI, PstI and HindIII sites.

After ligation of the NcoI/HindIII fragment of pPSAI.6 into the two digested vectors, sequence analysis confirmed the structure of the FIG. 2 plasmid constructs, designated pAP85 (the pKK233-2 expression vector) and pApoF (the pKT52 expression vector).

EXAMPLE II

Expression of AI Genomic Fragment in *E. coli*

*E. coli* JA221 (Nakamura, K., et al, J Mol Appl Genet 1:289 (1982)) (1 pp⁻/F'lacIQ) containing plasmid pKK233-2, pAP85 or pApoF were grown in M9 medium (Miller, J., *Experiments in Molecular Genetics*, Cold Spring Harbor Laboratory, Cold Spring Harbor, New York, 1972) supplemented with glucose (2 mg/ml), thiamine (10 μg/ml), $MgSO_4-7H_2O$ (250 μg/ml), $CaCl_2$ (11 μg/ml), tryptophan (20 μg/ml), leucine (20 μg/ml), methionine (2 μg/ml), ampicillin (100 μg/ml), and isopropyl-1-thio-D-galactopyranoside (IPTG, 1 mM).

At a cell density of approximately $5 \times 10^8$ cells/ml ($OD_{590}$ nm=0.5), 10 μCi/ml of L-[$^{32}$S]-methionine (>1000 Ci/mmole) was added. Following 30 sec of incubation, 1 ml of culture was removed, added to 0.34 ml of ice-cold 20% (w/v) trichloracetic acid (TCA) in a 1.5 ml Eppendorf centrifuge tube, vortexed, and incubated at 0° C. (on ice) for 30 minutes. The mixture was then centrifuged at 4° C. for 10 min in an Eppendorf centrifuge at 15,000× g. The supernatant was discarded and the pellet was washed once with 1 ml of ice-cold acetone, followed by centrifugation for 2 min. The acetone was aspirated off and the pellet allowed to air dry.

The dried TCA pellet was resuspended in 40 μl of 50 mM Tris-HCl, pH 6.8, 1 mM EDTA, and 1% (w/v) SDS. Ten μl of this resuspension was added to 10 μl of 2× SDS gel sample buffer (125 mM Tris-HCl, pH 6.8, 20% glycerol, 2% SDS, 2% β-mercaptoethanol, and 0.1% bromophenol blue), and incubated at 100° C. for 2 minutes.

The remaining 30 μl of the resuspension was brought to a 1 ml total volume by the addition of 970 μl of 50 mM Tris-HCl, pH 6.8, 0.15M NaCl, 0.1 mM EDTA, and 2% (v/v) Triton X-100. Two μl of sheep anti-h-apolipoprotein-AI-antiserum (obtained from Boehring Mannheim) was added to the suspension. The suspension was incubated at 0° C. on ice overnight. Following incubation, 50 μl of Pansorbin (10% (w/v) cell suspension, *Staphylococcus aureus* cells obtained from Calbiochem-Behring, La Jolla, CA) was added to the suspension, gently mixed, and incubation continued at 0° C. for 30 min. The suspension was centrifuged in the Eppendorf centrifuge for 2 min at 4° C. The supernatant was aspirated and the cell pellet resuspended in 0.5 ml of 50 mM Tris-HCl, pH 7.5, 5 mM EDTA, 0.5M NaCl, 0.5% (v/v) NP-40, and 1 mg/ml ovalbumin. The pellet was washed with vigorous vortexing, followed by centrifugation and aspiration of the supernatant. This washing procedure was repeated three additional times. Two further washes followed with 0.5 ml of 50 mM Tris-HCl, pH 7.5, 5 mM EDTA, 0.15M NaCl, and 0.5% (v/v) NP-40. The final cell pellet was resuspended in 50 μl of SDS gel sample buffer (75 mM Tris-HCl, pH 6.8, 10% (w/v) glycerol, 1% (w/v) SDS, 1% (w/v) β-mercaptoethanol, 0.05% (w/v) bromophenol blue), followed by incubation at 100° C. for 5 min. Cell debris was removed by centrifugation in an Eppendorf centrifuge for 5 min at room temperature.

The total and immunoadsorbed samples were subjected to SDS-polyacrylamide gel electrophoresis according to the method of Laemmli (Laemmli, U. K., Nature (London) 227:680 (1970)) in the presence of 6M urea. Sixteen cm long slab gels (1.5 mm thick) of 16% acrylamide were electrophoresed at 30 mAmp constant current until the bromophenol blue dye reached the bottom of the gel. Gels were fixed for 30 min in 30% (v/v) methanol, 10% (w/v) TCA, and 10% (v/v) acetic acid and treated with En³Hance obtained from New England Nuclear (Boston, Massachusetts) according to the manufacturer's directions, followed by drying and fluorography at −70° C. using Kodak XAR-5 X-ray film.

Figure 3:
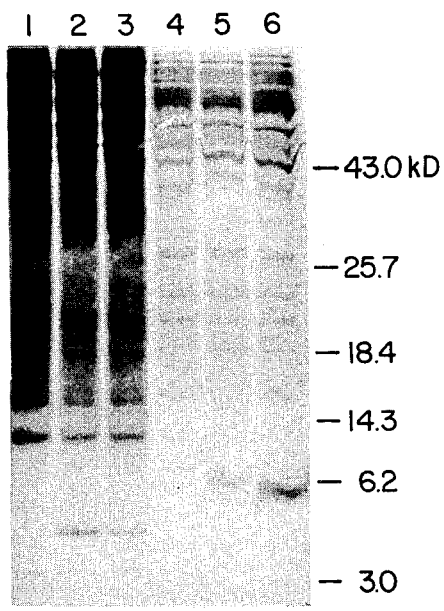
FIG. 3 is an autoradiographic analysis for the expression of cloned human apoAI C-terminal genomic fragment in *E. coli;*

A comparison of polypeptides extracted from cells containing plasmids pKK233-2, pAP85, and pApoF, labeled with L-[$^{35}$S]-methionine as shown in FIG. 3. A unique polypeptide migrating at a molecular weight of approximately 4500 daltons appears in lanes 2 and 3 which are protein patterns from cells containing plasmids pApoF and pAP85, respectively. Cells containing plasmid pKK233-2 (lane 1) do not have this unique peptide. The estimated molecular weight of the apoAI fragment peptide based on amino acid composition is 8,700 daltons. The discrepancy between measured and expected molecular weight may be due either to the lipophilic nature of the protein, which may effect its binding to SDS, or to a processing event which is taking place in the cell. This unique polypeptide is specifically immunoreactive to serum raised against apoAI (FIG. 3, lanes 5 and 6). ApoAI antiserum does not react with any unique polypeptides extracted from cells containing plasmid pKK233-2 (lane 4).

EXAMPLE III

Bacterial Vector with AI cDNA

Plasmid pBL13AI containing a full-length AI cDNA was prepared as described in Seilhamer, J. J., et al, supra. The plasmid (100 μg) was digested to completion with EcoRI for 3 hr at 37° C. The 965 base pair EcoRI fragment containing the apoAI cDNA was isolated on a 4% (w/v) nondenaturing polyacrylamide gel (Maniatis, et al, supra). The apoAI cDNA fragment was excised from the gel, electroeluted, and concentrated by ethanol precipitation. The resulting DNA pellet was dried in vacu and resuspended in $H_2O$. This EcoRI fragment was further digested with Sau3A for 30 min at 37° C. with a DNA-to-enzyme ratio of 1 μg:2 units. The resulting Sau3A fragments were separated as described above. The 783 base pair partial fragment was isolated and concentrated as described above.

Figure 4:
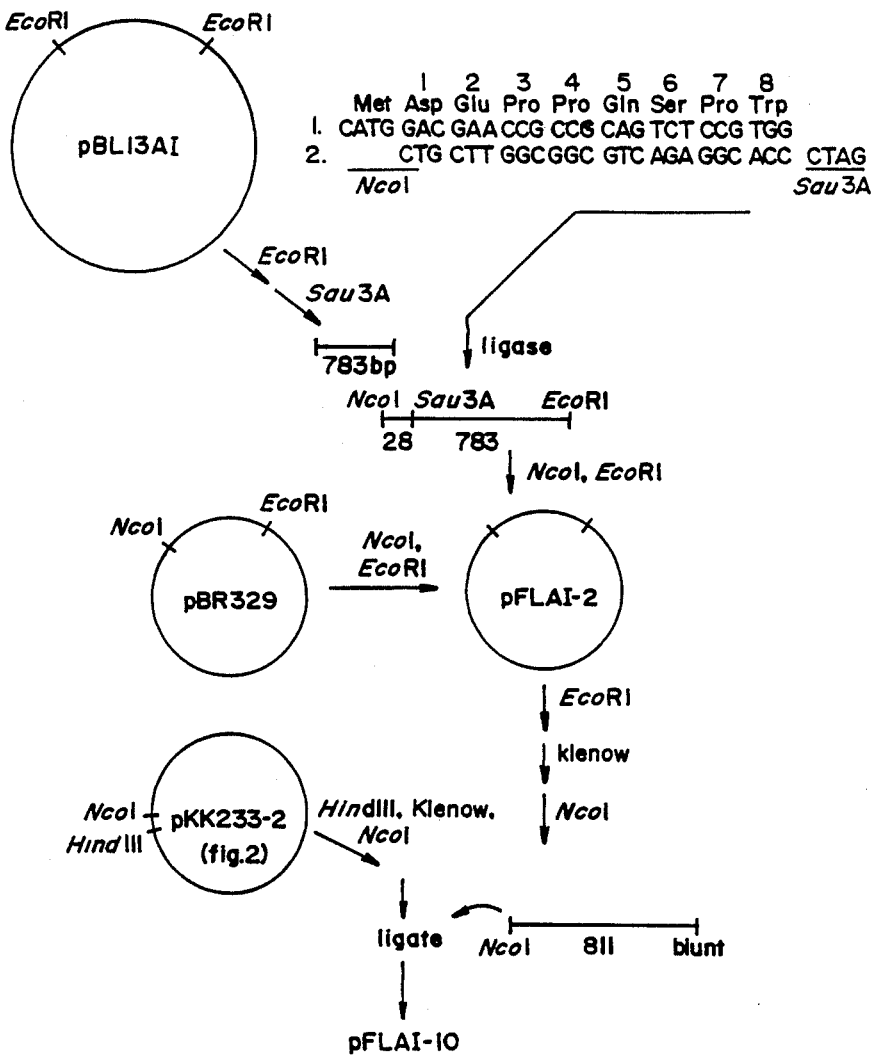
FIG. 4 shows the construction of a bacterial vector, designated pFLA1-10, designed for expression of mature human apoAI in *E. coli;*

Two complementary oligonucleotides (FIG. 4) containing the coding sequence of the first 8 amino acids of mature apoAI protein were synthesized on a Biosearch SAM I DNA Synthesizer (Biosearch, San Rafael, CA) according to the manufacturer's instructions. The oligonucleotides were kinased with $^{32}$P-ATP using T4 polynucleotide kinase (Maniatis, et al, supra). The two oligonucleotides (1 ng each) were mixed, boiled for 2 min, and allowed to hybridize at RT for 60 min. The hybridized oligonucleotides were ligated to 25 ng of Sau3A partial apoAI cDNA fragment with the addition of T4 DNA ligase by the method of Maniatis, et al, supra. After ligation, the mixture was digested to completion with EcoRI and NcoI. Products were separated on a 5% nondenaturing polyacrylamide gel. The 811 base pair fragment corresponding to full-length coding sequence of mature apoAI protein was excised. The DNA was eluted from the gel slice in 10 mM Tris-HCl, pH 8, 1 mM EDTA, 0.4M NaCl with agitation at 37° C. overnight and concentrated by ethanol precipitation. The NcoI-EcoRI fragment was then ligated into pBR329 vector. The resulting plasmid, shown in FIG. 4, is designated pFLAI-2.

In order to confirm the correct DNA sequence through the constructed oligonucleotide site, an RsaI fragment of pFLAI-2 encompassing the first 56 base pairs of the coding region for mature apoAI, as well as 112 base pairs downstream into pBR329 was sequenced by the dideoxy method (Messing, J., et al, Gene 19:259 (1982) and Sanger, et al, Proc Natl Acad Sci (U.S.A.) 74:5463 (1977)).

The NcoI-EcoRI construct was the ligated into the bacterial expression vector pKK233-2 of FIG. 2. Plasmid pFLAI-2 (10 μg) was digested to completion with EcoRI and the ends filled in the method of Maniatis et al, supra, with E. coli DNA Polymerase I, Klenow fragment, and the addition of 0.5 mM dATP and dTTP. The blunted DNA was then phenol/chloroform extracted, and concentrated by ethanol precipitation. The blunted DNA was further digested to competition with NcoI. The 811 base pair fragment containing the coding region of mature apoAI was purified on a 5% non-denaturing acrylamide gel and concentrated as described above. The NcoI blunt fragment was then ligated using T4 DNA ligase (Maniatis et al, supra) into pKK233-2 which was cut with HindIII, blunted, phenol extracted, and cut with NcoI. The resulting plasmid is designated pFLAI-10 (FIG. 4).

EXAMPLE IV

Expression of Full-Length ApoAI in E. coli

E. coli JA221 (1 pp−/F'lacI$^Q$) containing plasmids pKK233-2 or pFLAI-10 (Example III) were grown and labelled in M9 medium (Miller, J., Experiments in Molecular Genetics, Cold Spring Harbor Laboratory, Cold Spring Harbor, New York, 1972), as in Example II. Following 30 sec of incubation with [$^{35}$S]-methionine, 1 ml of culture was removed and washed TCA precipitable material was obtained, as in Example II.

The pellet was resuspended in 50 μl of 5 mM Tris-HCl, pH 6.8, 1 mM EDTA, and 1% (w/v) SDS, and incubated at 100° C. for 3 min. An aliquot equal to $2 \times 10^5$ cpm was added to the SDS gel sample buffer of Example II, and incubated 100° C. for 2 min. A second aliquot equal to $2 \times 10^6$ cpm was brought up to 1 ml total volume by the addition of 5 mM Tris-HCl, pH 6.8, 0.15M NaCl, 0.1 mM EDTA, and 2% (v/v) Triton X-100. 2 μl of rabbit antiserum raised against human apoAI was added to the suspension. The suspension was incubated at room temperature for 30 min and further incubated on ice overnight. Following incubation, 50 μl of a 10% (w/v) Protein A Sepharose CL-4B (obtained from Sigma, St. Louis, MO) suspension in 50 mM Tris-HCl, pH 7.5, 5 mM EDTA, 0.15M NaCl, 0.5% (v/v) NP-40, and 1 mg/ml ovalbumin was added. Incubation continued with gentle agitation for 60 min at 4° C. The suspension was centrifuged 15,000× g for 3 min at 4° C. The supernatant was aspirated, and the Sepharose beads were washed 5 times with 0.5 ml 50 mM Tris-HCl, pH 7.5, 5 mM EDTA, 0.5M NaCl, 0.5% (v/v) NP-40, 1 mg/ml ovalbumin, 2 times with 50 mM Tris HCl, pH 7.5, 5 mM EDTA, 0.15M NaCl, 0.5% (v/v) NP-40, and once with 10 mM Tris-HCl, pH 7.5. The pellet was then resuspended in 30 μl of SDS gel sample buffer and incubated at 100° C. for 5 min.

The total and immunoadsorbed samples were subjected to SDS-polyacrylamide gel electrophoresis according to the method of Laemmli (Laemmli, U. K., supra). Sixteen cm slab gels (0.7 mm thick), 10–20% acrylamide gradients, were electrophoresed at 15 mAmps until the BPB dye reached the bottom of the gel. Gels were fixed in 25% (v/v) methanol, 10% (w/v) TCA and 10% (v/v) acetic acid for 30 min. Gel autoradiography was performed as in Example II.

Figure 5:
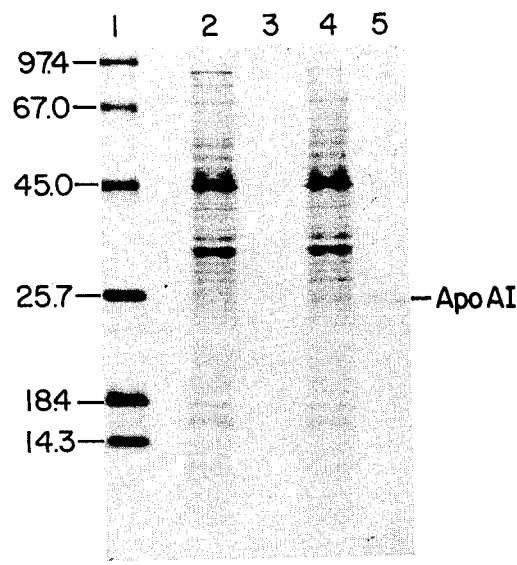
FIG. 5 is an autoradiogrpahic analysis of the expression of cloned human apoAI in *E. coli;*

A comparison of polypeptides extracted from cells containing plasmids pKK233-2 and pFLAI-10 is shown in FIG. 5. A unique polypeptide migrating at a molecular weight of 25,000 daltons appears in cells harboring the plasmid pFLAI-10 (lane 4). This unique protein is not present in cells harboring plasmid pKK233-2 (lane 2). Commercially prepared mature apoAI protein (Calbiochem-Behring, La Jolla, CA) also migrates at 25,000 daltons, identically to the bacterial product. It should be noted that the calculated molecular weight of mature apoAI protein is 27,000 daltons, but the hydrophobic nature of this protein causes it to migrate at an apparent molecular weight of 25,000 daltons in this gel system. This unique polypeptide is specifically immunoreactive to serum raised against apoAI (lane 5). ApoAI antiserum does not react with any unique proteins from cells harboring plasmid pKK233-2 (lane 3).

EXAMPLE V

Yeast Vector with ApoAI cDNA

A yeast library in the E. coli-yeast shuttle vector YEp13 (Nasmyth, K., et al, Cell 19:753 (1980)) was screened using a 5'-$^{32}$P end-labeled oligodeoxynucleotide 5'-dCCTGGCCAACCAATG-3' (Maniatis et al, at pp. 324–325). Plasmids containing inserts of yeast DNA hybridizing to this oligonucleotide were subsequently isolated. One of these plasmids contained an insert of approximately 15 kb of yeast DNA, and was shown to contain the 1.7 kb EcoRI fragment containing the alpha-factor gene as described by Kurjan and Herskowitz (Kurjan, J., et al, Cell 30:933 (1982)). The end of the 1.7 kb EcoRI fragment were made blunt by incubation with DNA Polymerase I (Klenow fragment) and BamHI linkers using T4-DNA ligase (Maniatis, et al, at pp. 113–114, 116, 392–394). The BamHI ends were made cohesive by digestions with Bam HI restriction endonuclease, subsequently ligated into the BamHI site of the yeast-E. coli shuttle plasmid pCV7-Hin2 (Broach, J. R., et al, Cell 21:503 (1980)). A deletion around the HindIII site of the plasmid CV7 was made by HindIII digestion, treatment with exonuclease III, treatment with S1 nuclease, and religations with T4-DNA ligase to generate the plasmid pCV7-Hin2, all using the method described in Maniatis et al, supra. This plasmid containing the yeast alpha-factor gene is diagramed in FIG. 6, and designated YEp-α-8.

Figure 6:
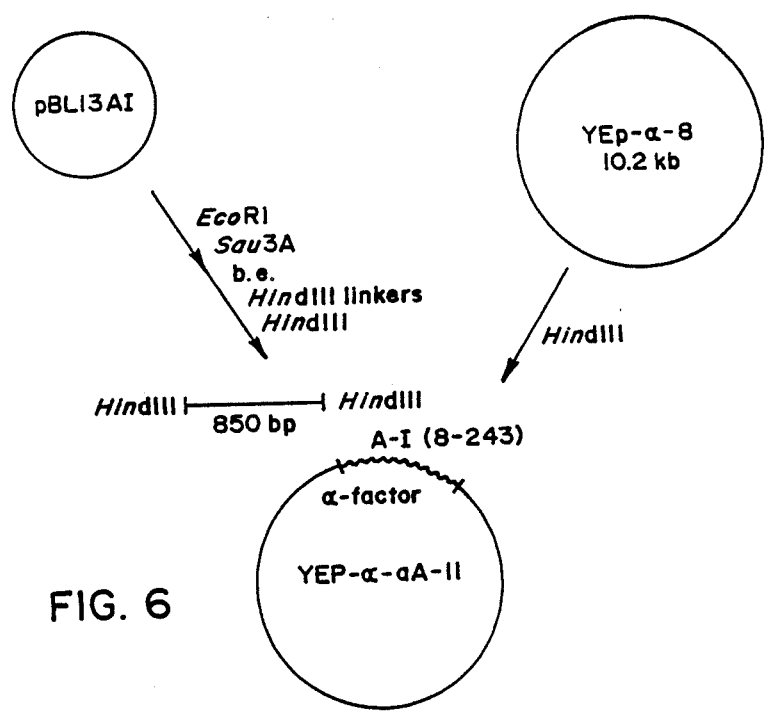
FIG. 6 shows the construction of a yeast vector, designated YEp-a-aA-11, designed for expression of mature human apoAI in *S. cerevisiae;*

A fragment of DNA from pBL13AI (Example III) encoding the entire mature apoAI sequence minus the first eight amino acids was inserted into the unique HindIII cloning site of YEp-α-8 (FIG. 6). With reference to the figure, digestion of pBL13AI (10 μg) with EcoRI endonuclease followed by partial digestion with Sau3A endonuclease produced a 0.78 kb Sau3A-EcoRI fragment the ends of which were made blunt with DNA Polymerase I (Klenow fragment) and synthetic HindIII linkers (pCCAAGCTTGG) using T4 DNA ligase (Maniatis, et al, supra, pp. 113–114, 392–394). The HindIII ends were made cohesive by digestion with HindIII endonuclease and ligated into HindIII-cleaved YEp-α-8 which had been treated with alkaline phosphatase to remove its 5' phosphate moieties (Maniatis, et al, supra, pp. 366-369). With insertion into the yeast vector, amino acid number eight of mature apoAI is restored by the HindIII linker, allowing for coding of amino acids 8-243 of mature apoAI.

Expression vector YEp-α-aA-11 (FIG. 6) with the apoAI insert in the correct orientation encodes a chimeric protein consisting of factor signal/leader peptide and almost the entire mature apoAI sequence (amino acids 8-243). Expression vector YEp-α-aA-5 with the insert in the reverse orientation encodes a chimeric protein with the same signal/leader peptide and a protein unrelated to apoAI.

EXAMPLE VI

Expression of ApoAI Full-Length cDNA in *S. cerevisiae*

DNA was prepared from *E. coli* cultures containing the plasmids YEp-α-8, YEp-α-aA-11, and YEp-α-aA-5 (Example V) and was used to transform yeast strain W301-18A (α ade 2-1, trp 1-1, leu 2-3, -112, can 1-100, ura 3-1, his 3-11, -15) (Kramer, et al, Proc Natl Acad Sci (U.S.A.) 81:367 (1984)) to Leu 2 prototrophy. Yeast strains were grown on standard media (Sherman et al, Methods in Yeast Genetics, Cold Spring Harbor Press, Cold Spring Harbor, New York). Plasmid DNA from *E. coli* was also recloned into M13 for sequencing and confirmation of the α-factor apoAI DNA constructions (Messing, J., et al, Gene 19:259 (1982) and Sanger, et al, Proc Natl Acad Sci (U.S.A.) 74:5463 (1977)).

Yeast cultures Y9-1 (YEp-α-8/W301), Y9-2 (YEp-α-aA-11/W301), and Y9-3 (YEp-α-aA-5/W301) were maintained in synthetic medium lacking leucine. Saturated overnights were diluted back in fresh media with the addition of 100 μg/ml BSA (bovine serum albumin) to OD600 nm=1.5. Cultures were shaken at 30° C. for 30 min at which time 200 μCi/ml of L-[$^{35}$S]-methionine (>1000 Ci/mmole, Amersham Corp., Chicago, ILL) was added. Growth was allowed to continue for 4 hr, at which time PMSF (phenylmethylsulfonylfluoride) was added to 1 mM. Cultures were centrifuged at 5,000 rpm for 5 min, and the cell pellet discarded. Medium supernatant proteins were concentrated by the addition of ice cold TCA to a final concentration of 10%. The supernatant was incubated on ice for 30 min, centrifuged for 15 min at 4° C. in an Eppendorf centrifuge at 15,000× g, and the pellet was washed with 1 ml of ice cold acetone. The final is dried in vacu, resuspended in 50 mM Tris-HCl, pH 6.8, 1 mM EDTA, 1% (w/v) SDS, and incubated at 100° C. for 3 min. 10 μl of this resuspension was added to 10 μl of 2× SDS gel sample buffer.

The remaining 40 μl was brought up to 1 ml by the addition of 960 μl of 50 mM Tris-HCl, pH 6.8, 1 mM EDTA, and 2% (v/v) Triton X-100. Two μl of rabbit antiserum raised against human apoAI was added to the suspension. The suspension was then incubated, reacted with Protein A Sepharose, and washed as described in Example IV. The total and immunoadsorbed samples were subjected to SDS-polyacrylamide gel electrophoresis as described in Example IV.

Figure 7:
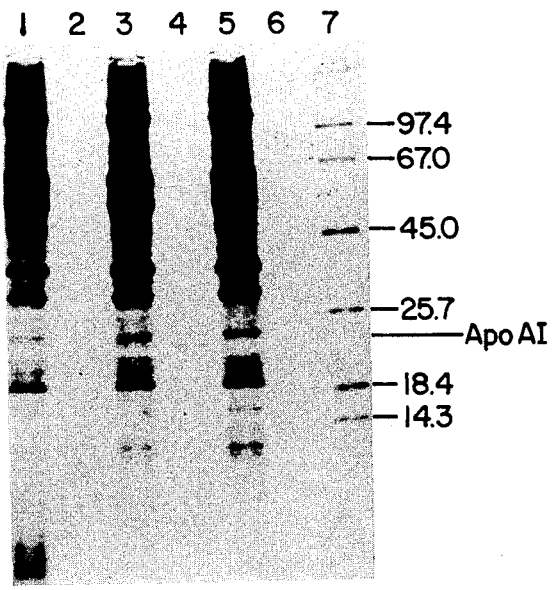
FIG. 7 is an autoradiographic analysis of the expression of cloned human apoAI in *S. cerevisiae;*

A comparison of polypeptides extracted from the media of *S. cerevisiae* cultures carrying the expression constructs is shown in FIG. 7. A unique polypeptide migrating at a molecular weight of approximately 23,000 daltons appears in cultures of yeast carrying the alpha factor expression vector with the apoAI cDNA insert in the correct orientation (Y9-2, lane 3). This unique protein is not present in yeast carrying the α factor expression vector only (Y9-1) or the apoAI cDNA insert in the wrong orientation (Y9-3) (lanes 1 and 5, respectively). This unique protein is specifically immunoreactive with rabbit antiserum raised against human apoAI (lane 4). Proteins from the other yeast cultures Y9-1 and Y9-3 have no specific reaction with apoAI antiserum (lanes 2 and 6, respectively). The recombinant α factor-apoAI cDNA expression vector (YEp-α-aA-11) encodes for an apoAI protein 7 amino acids shorter from the N-terminus than mature apoAI (only amino acids 8-243 are encoded). This accounts for the fact that the apoAI product synthesized in yeast cultures migrates ahead of mature apoAI produced by bacterial expression (Example IV and FIG. 5) and by mammalian-cell expression (Example VIII and FIG. 9 below).

EXAMPLE VII

Construction of Mammalian-Cell Vector for AI Expression

Figure 8:
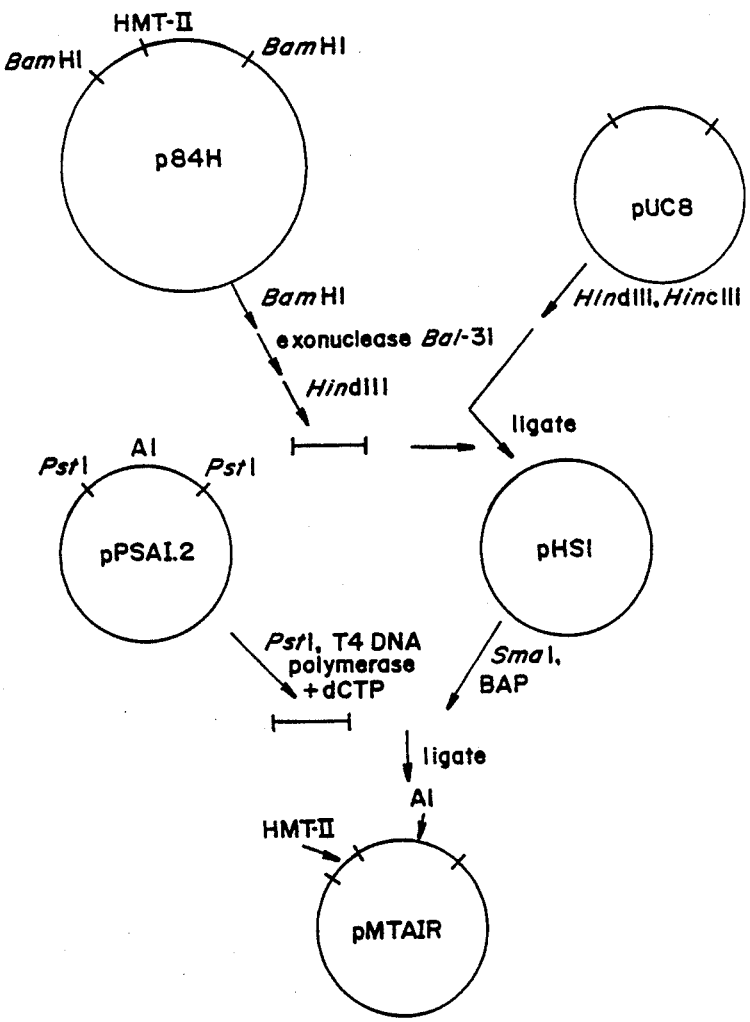
FIG. 8 shows the construction of a mammalian-cell vector, designated pMTAIR, designed for expression of mature human apoAI in Chinese hamster ovary (CHO) cells.

To facilitate the expression of apoAI in mammalian cells, a hybrid gene was constructed in which the coding segment for apoAI was fused to a powerful regulated promoter derived from the human metallothionein II (hMT-II) gene. This was performed in two steps, which are illustrated in FIG. 8. First, an expression vector was prepared. The expression vector, pHSI, carried 840 nucleotide base pairs of hMT-II sequence (Karin, M., et al, Nature 299:797 (1982)) from a naturally occurring HindIII restriction site at base −765 from the start of transcription to base +70, located in the 5' untranslated region adjacent to the coding region. pHSI also carries a region into which coding sequences may be inserted. To construct pHSI, the plasmid p84H (Karin, et al, supra), which carries the hMT-II gene, was digested to completion with restriction endonuclease BamHI followed by treatment with exonuclease Bal-31 to remove terminal nucleotides. Following digestion with HindIII, the products of this reaction were ligated into plasmid pUC8 (Messing, J., et al, supra) which had been opened with HindIII and HincII digestion. One of the resulting plasmid recombinants had the composition of pHSI as determined by nucleotide sequencing.

To complete the construction of the hybrid gene, the PstI fragment spanning the apoAI gene was isolated from plasmid pPSAI.2 (Example I) by digestion with PstI followed by polyacrylamide gel purification. The PstI fragment extends from a point in the 5' untranslated region through the entire coding sequence (with introns) and terminates beyond the poly A addition site. The purified fragment was blunt ended by digesting away the single-stranded 3' termini with T4 DNA polymerase in the presence of dCTP. The flush-ended molecules were then ligated to the expression vector plasmid pHSI, which had been opened by restriction with SmaI, followed by treatment with bacterial alkaline phosphatase. The products of the reaction were introduced into *E. coli* MC1061, and the recombinant, pMTAIR was identified. In the resulting plasmid, pMTAIR, the apolipoprotein AI coding sequences are in position to be expressed by hMT-II promoter. The plasmid is contained in the deposited CHO cells, CRL #8911.

EXAMPLE VIII

AI Synthesis in CHO Cells

Plasmid pMTAIR from Example VII was introduced into the Chinese hamster ovary (CHO:KI) line of cultured cells (growing in McCoy's 5A medium with 10% fetal bovine serum) by co-transformation with pSV2:NEO (Southern, P., et al, J Mol Appl Genet 1:327 (1982)), a plasmid carrying a functional gene conferring resistance to the neomycin analog G418. Five hundred ng of pSV2:NEO and 5 μg of pMTAIR were applied to a 60 mm dish of cells in a calcium phosphate-DNA co-precipitate according to standard protocols (Wigler, M., et al, Cell 16:777 (1979)) with the inclusion of a two min "shock" with 15% (w/v) glycerol after 4 hr exposure to the DNA. A day later the cells were subjected to exposure to G418 at 1 mg/ml. This procedure yielded a pool of G418-resistant colonies most of which had also acquired stable inheritance of pMTAIR.

CHO:KI cells transformed with either plasmid pMT401 (control, hMT-II plasmid with no foreign insert) or pMTAIR were grown to 70% confluency in 9.6 cm$^2$ wells in standard medium (RPMI plus 10% dialyzed fetal bovine serum). Cells were preinduced with $1.5 \times 10^{-4}$M ZnCl$_2$ for 7 hr, at which time 0.15 μg/ml L-[$^{35}$S]-methionine was added. Cells were incubated in the presence of label overnight, at which time medium was harvested, and cell debris removed by low speed centrifugation.

One portion of the medium ($1 \times 10^5$ cpm) was added to SDS gel sample buffer and incubated at 100° C. for 2 min. A second portion of medium ($5 \times 10^5$ cpm) was brought up to 1 ml final volume by the addition of 50 mM Tris-HCl, pH 6.8, 0.15M NaCl, 0.1 mM EDTA, and 2% (v/v) Triton X-100. Two μl of rabbit antiserum raised against human apoAI was added to the suspension. The suspension was then incubated, reacted with Protein A Sepharose, and washed as described in Example IV. The total and immunoabsorbed samples were subjected to SDS-PAGE as described in Example IV.

Figure 9:
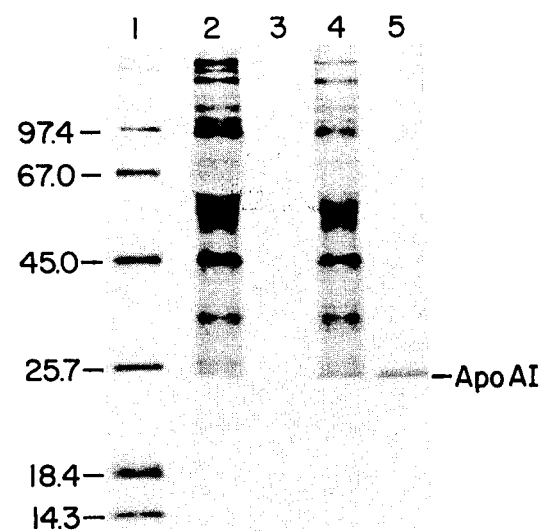
FIG. 9 is an autoradiographic analysis of the expression of cloned human apoAI in CHO cells.

A comparison of polypeptides extracted from medium of CHO cells transformed with the recombinant plasmids pMT401 and pMTAIR is shown in FIG. 9. A unique polypeptide migrating at molecular weight of 25,000 daltons appears in the medium from cells transformed with pMTAIR (lane 4). This unique protein is specifically immunoreactive to serum raised against apoAI (lane 5). There are no unique polypeptides present in lane 2, proteins extracted from cells transformed with pMT401, nor do any proteins immunoreact with apoAI antiserum, lane 3. Commercially prepared mature apoAI co-migrates with the mammalian expression product, and both migrate an apparent molecular weight of 25,000 daltons due to the lipophilic nature of apoAI and the gel system used. Protein in FIG. 9 represents apoAI being made from a transformed pool of CHO:KI cells (CHO/pMTAIR).

EXAMPLE IX

High-Producing CHO Cells for AI Production

The pool of transformed CHO:KI cells from Example VIII was plated at low density (100–200 cells/ml) in standard medium (DMEM 21/Coon's F-12 plus 10% FBS), producing individual clonal colonies after 4–7 days growth at 37° C. The colonies were separately picked and grown in the above medium to a cell density of about 10$^6$ cell/ml.

The clonal cultures were individually assayed for AI expression by dot-blot Western, using the method described in Jahn, et al, Proc Natl Acad Sci (U.S.A.) 81:1684 (1984). Individual clones were seeded at 25% confluency in 12 well dishes in 1.5 ml DMEM21/Coons F12 plus 10% FBS. After 24 hr, the cells were washed once with 1 ml PBS and fresh medium containing $1 \times 10^{-4}$M Zn sulfate was added to begin preinduction. At 16 hr after preinduction, the cells were washed twice with 1 ml PBS and refed with 0.65 ml serum-free medium containing $3 \times 10^{-5}$M Zn sulfate and $3 \times 10^{-5}$M Fe sulfate. After 48 hr of serum-free induction, the media was harvested and centrifuged at 1000 rpm for 5 min to remove cell debris. 0.5 ml serum-free conditioned medium was applied to each well onto a nitrocellulose filter, (Schleicher & Schuell, Keene, NH) using a dot-blot microfiltration apparatus (Bio-Rad Laboratories, Richmond, CA). Blots were probed with sheep antiserum raised against human apoAI (Boehring-Mannhein) at 1:50 dilution. Antigen-antibody complex was detected with I$^{125}$ labeled Protein A (Amersham). About 200 clonal colonies were examined.

Figure 10:
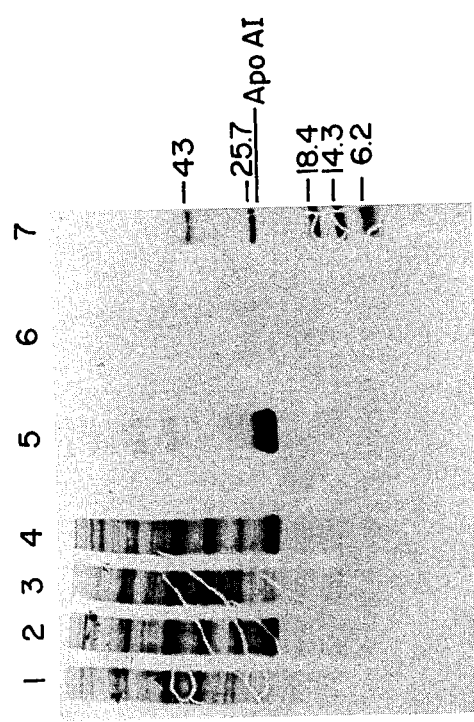
FIG. 10 shows gel electrophoretic patterns of proteins expressed by CHO cells transformed with control and pMTAIR vectors, and the proteins, including apoAI, which float with lipid emulsion particles.

One of the AI high-producing cells, designated clone 104, was examined for AI expression, substantially according to methods described in Example VIII. FIG. 10 shows SDS gel electrophoresis patterns of the proteins produced in the system. Lanes 1 and 3 are total S$^{35}$-methionine-labeled secreted proteins from CHO-pMT401 (control) cells, and lanes 2 and 4, from CHO:pMTAIR cells of clone 104. As seen, apoAI secreted from clone 104 is easily identifiable in the total secreted medium proteins without immunoprecipitation. This clone is producing apoAI at approximately a 30-fold higher level than the pool cells.

EXAMPLE X

Large-Scale AI Production

A second high-producing CHO:pMTAIR clone from Example IX, producing the same level of apoAI as clone 104 and designated clone 143, was used for large-scale AI production in roller bottles. The clone 104 is the high-producing CHO cell line identified as CRL 8911.

A 10 cm plate of clone 143 was grown to confluence in 10 ml DMEM-21/Coon's F-12 (Gibco, Irvine, CA) plus 10% fetal bovine serum (Gibco) medium. The cells in the plate were washed once with 2 ml phosphate buffered saline (PBS), trypsinized, and suspended in 250 ml DMEM-21/Coon's F-12 medium containing 10% FBS and 15 mM HEPES buffer in an 850 cm$^2$ roller bottle. After 2 days of incubation at 37° C., zinc sulfate was added to a final concentration of $1 \times 10^{-4}$M. At day 3, the cells were switched to serum-free DMEM-21/Coon's F-12 medium containing $6 \times 10^{-5}$M zinc sulfate and $3 \times 10^{-5}$M iron sulfate, marking the beginning of the production period.

The cells were cultured for 2 days following the medium switch (day 2 in Table I), and the conditioned medium harvested by low-speed centrifugation to separate cell debris from spent medium. The cell medium was fractionated by SDS gel electrophoresis, as in Example VIII, and the gel, after staining with Coomassie Brilliant Blue, was scanned optically to quantitate the amount of apoAI protein in the cell-free medium, using a purified AI standard obtained from Calbiochem (La Jolla, CA) to produce a gel-staining calibration curve.

Fresh serum-free medium containing $7\times10^{-5}$M zinc (and $3\times10^{-5}$M iron sulfate) was added to the cultured roller bottle and cultured for an additional 2 days (day 4 in Table I). Cell-free conditioned medium was again harvested at day 6 and examined for AI concentration, as above, and fresh medium containing $7.5\times10^{-5}$M Zn was replaced in the roller bottle. The procedure was repeated at days 6–11, as indicated in Table I, with $8\times10^{-5}$ Zn being added at day 6 and thereafter. The concentration of zinc shown in the middle column in the table is that which the cells were exposed to from the period between harvests. Thus, the cells were exposed to $6\times10^{-5}$ Zn between production days 0–2, and so forth. The amount of AI produced, expressed in μg/ml/day, is shown at the right in the table. As seen, AI expression increased over the first 8 days, then plateaued at about 30 μg/ml/day after day 8.

TABLE I

| Production Time (days) | [Zn] | AI Production (μg/ml/day) |
|---|---|---|
| 2 | $6 \times 10^{-5}$M | 5–7.5 |
| 4 | $7 \times 10^{-5}$M | 10 |
| 6 | $7.5 \times 10^{-5}$M | 15 |
| 7 | $8 \times 10^{-5}$M | 20 |
| 8 | $8 \times 10^{-5}$M | 30 |
| 9 | $8 \times 10^{-5}$M | 30 |
| 10 | $8 \times 10^{-5}$M | 30 |
| 11 | $8 \times 10^{-5}$M | 30 |

EXAMPLE XI

Cloning and Expression of AII in CHO Cells

A human fetal liver cDNA library in λgt10 prepared as in Huynh, V. T., et al, DNA Cloning Techniques: A Practical Approach (IRL Press, Oxford, 1984) was probed with a 45-base pair oligonucleotide coding for amino acid residues 140–164 of human apolipoprotein AII (AII) (see Sharpe, C. R., et al, Nucl Acids Res 12:3917 (1984)) of 750,000 recombinants which were screened, and 10 positive were obtained. One of these, designated λAII, had a 440 base EcoRI insert corresponding to the full-sequence AII cDNA (Sharpe, et al, supra) plus ~20 bases of 5' untranslated region. The EcoRI insert was isolated from the phage and cloned into pHSI.

Two versions, one with the AII insert in the correct orientation (pHSI/AII) and one in the incorrect orientation (pHSI/incorrect), along with pHSI alone, were each transfected into CHO cells and selected with G418. The cells were labelled with $^{35}$S-methionine and 0.5 ml of medium immunoprecipitated with 5 μl of rabbit anti-human apoAII antiserum obtained from Boeringer-Mannheim (Indianapolis, IN).

Figure 11:
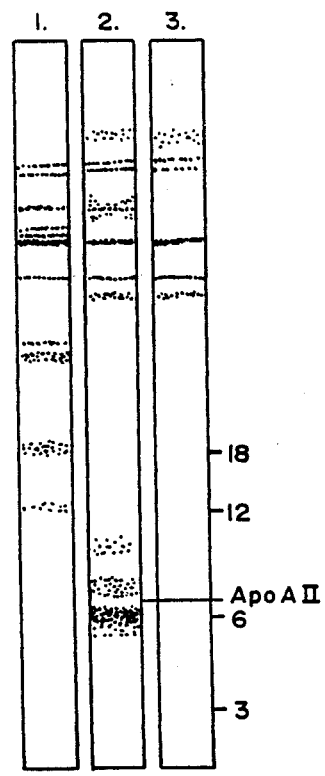
FIG. 11 is an autoradiographic analysis of the expression of cloned human apoAII in CHO cells.

The secreted proteins were analyzed by SDS gel electrophoresis, as in Example II, with the results shown in FIG. 11. Lanes 1, 2, and 3 are cell-free proteins from CHO cells transformed with pHSI (control), pHSI/AII, and pHSI/incorrect, respectively. As seen, the pHSI/AII transformed cells produce two low-molecular peptides of about 6,000–8,000 dalton molecular weight which are not seen in the two controls. The larger of the two pHSI/AII bands may be pro AII (78 amino acids), the other being mature AII (73 amino acids) or the different molecular weights may represent different degrees of glycosylation.

EXAMPLE XII

Cloning and Expression of AI Fragment in CHO Cells

Figure 12:
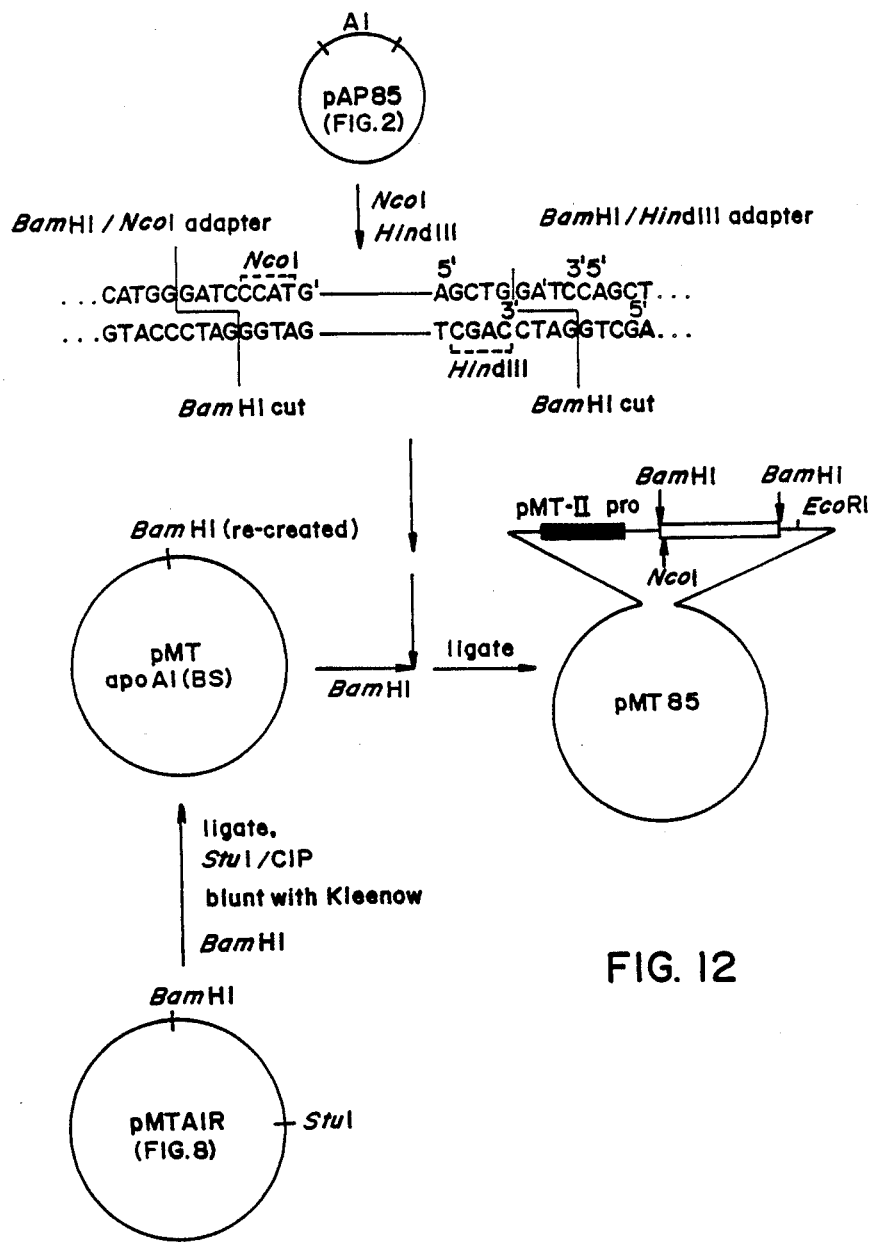
FIG. 12 shows the construction of a mammalian-cell vector, designed for expression of cloned human apoAI C-terminal genomic fragment in CHO cells.

An expression system capable of producing apoAI (110–187) in CHO cells is constructed as described here. The plasmid pAP85 containing the apoAI (110–187) fragment is cut with NcoI and HindIII and the insert containing the DNA coding for Met-apoAI (110–187)-Stop is isolated. The insert is blunted and ligated to the BamHI-NcoI adapter 5'-CATGGGATCC and the BamHI-HindIII adapter 5'-AGCTGGATCC at the 5' NcoI site and the 3' HindIII site, respectively. The DNA adapters are cut back with BamHI and the modified insert is purified by gel electrophoresis. The BamHI fragment is then ligated to the BamHI site of pMT apoAI (BS), the metallothionein expression plasmid which contains the 3' untranslated region of apoAI which includes a transcription termination signal, as described in detail in co-owned patent application Ser. No. 680,358, and incorporated herein by reference. As seen in FIG. 12, the plasmid is formed by digesting the pMTAIR vector from Example VII (on deposit) first with BamHI, and after blunt-ending with Klenow fragment, further digesting with StuI and treating with CIP. The ligation produces the desired pMT apoAI (BS) vector. The plasmid containing the insert in the correct orientation can be determined by restriction mapping. The plasmid containing the insert in the correct orientation is used to transfect CHO cells and high-producing clones selected as described.

EXAMPLE XIII

ApoAI Separation/Endogenous Lipid

Culture medium from the CHO:pMTAIR clone 143 cells in Example X was used. The medium was adjusted to a density of 1.125 g/ml by addition of solid potassium bromide, then centrifuged at 38K rpm for 18 hours in a swinging-bucket rotor. The top fraction was then removed by a conventional slicing method, and dialyzed extensively against saline. The material, when examined by SDS gel electrophoresis as in Example VIII, gave a prominent band in the 25,000 molecular weight range, corresponding to apoAI. Between about 10%–20% of the total apoAI produced by the CHO:pMTAIR cells was in the upper fraction, as judged by the relative staining intensities of the 25,000 molecular weight bands on SDS gels from the upper and lower centrifugation bands.

Figure 13:
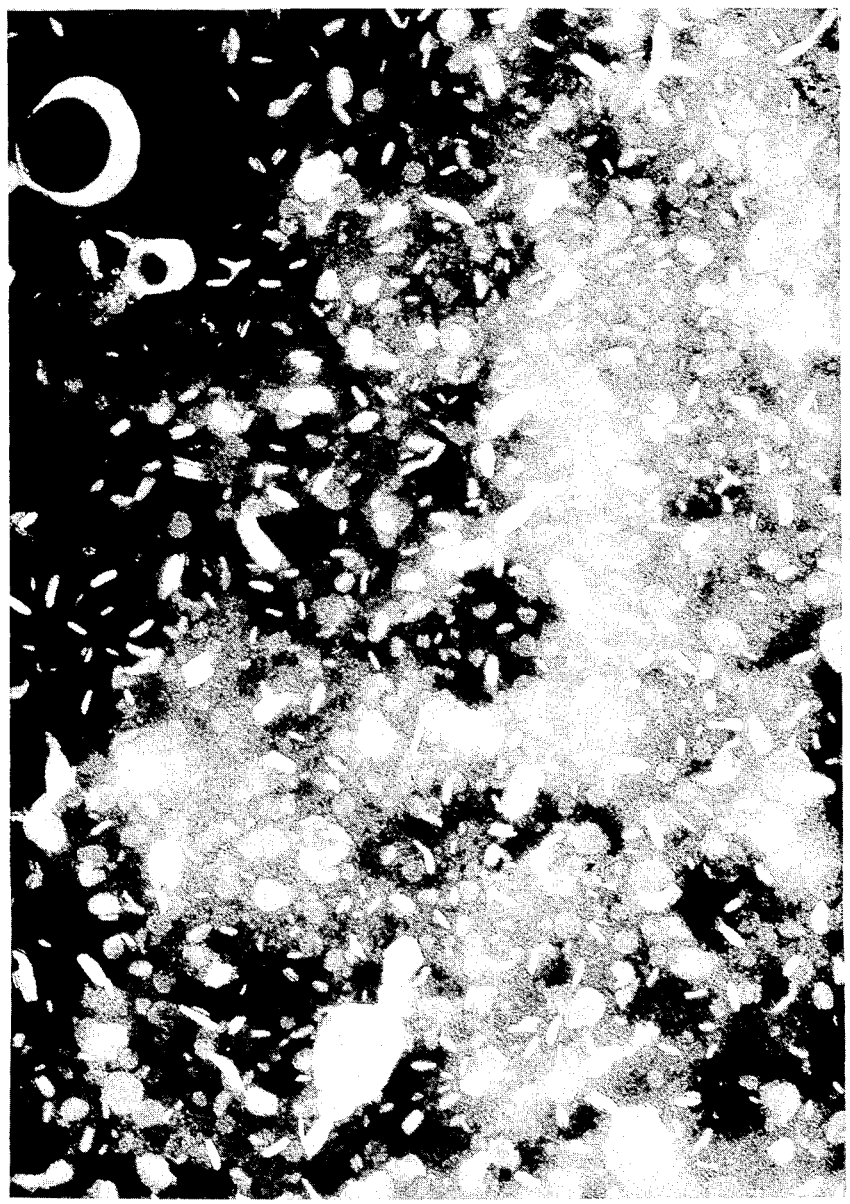
FIG. 13 is a negative-stain electron micrograph of lipoprotein complexes formed in accordance with the invention.

Electron micrograph of the top-fraction material shows the presence of numerous disc-shape structures characteristic serum of apoAI/phospholipid complexes, as shown in FIG. 13 (described in Hamilton, R. L., et al, J Clin Invest 58:667 (1976)).

EXAMPLE XIV

ApoAI Separation/Added Lipid Emulsion

INTRALIPID, obtained from Cutter Labs (Berkeley, CA) was used as the substrate to bind the apolipoprotein ligand. INTRALIPID is an artificial lipid emulsion composed of soybean triacylglycerol and egg lecithins. The mesophase, or phospholipid-rich portion of the emulsion was removed by ultracentrifugal floatation in a discontinuous sucrose gradient. The bottom layer contained 2 ml of emulsion, 0.6 g sucrose and saline to give a final volume of 4 ml a density of 1.06 g/ml. This layer, in a polyallomer tube of a Beckman SW41 rotor, was overlayed with 6 ml of an NaCl solution of d=1.02 g/ml. Finally a third layer was made of 2 ml of saline solution of d=1.006 g/ml. Centrifugation was at 28,000 rev/min at 10° C. for 60 minutes.

After centrifugation, the triglyceride rich emulsion on the top of the gradient was separated from the infranatant solution by the tube slicing technique using a Beckman slicer.

High-producing CHO:pMTAIR clone 143 from Example IX and control CHO:pMT401 cells were cultured in roller bottles, as described in Example X. The culture medium was concentrated 100 times by ultrafiltration using an Amicon YM 10 membrane. The concentrated medium was incubated with purified INTRALIPID and centrifuged as described for INTRALIPID except that only one step centrifugation was used. Lipid-to-protein ratios of either 0.1, 0.3, or 0.6 ml of concentrated medium per ml INTRALIPID were used.

A sample from each top fraction was delipidated and fractionated by SDS-PAGE. The Coomassie-stained gels are shown in FIG. 15. Bands 1, 2, and 3 are the gel patterns for the INTRALIPID fraction incubated with 0.1, 0.3, or 0.6 ml concentrated medium, respectively. Lane 4 is the non-lipid-bound protein fraction. As seen, (in the INTRALIPID bound fractions), apoAI is the only major protein that is separated with the less dense INTRALIPID fraction, and increasing quantities of medium yield increasing amounts of purified apoAI. The purity of apoAI was about 95%, as determined by staining density on the gels.

The unbound fraction contains some apoAI and other contaminating proteins secreted from the CHO cells.

EXAMPLE XV

AI Purification

Figure 14:
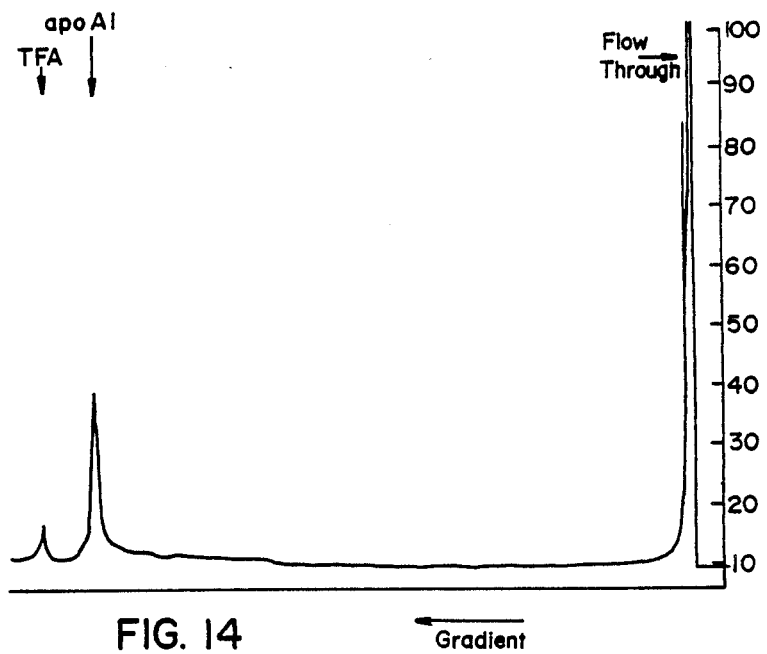
FIG. 14 is an ultraviolet scan of the elution profile from an HPLC column used to purify recombinant mature human apoAI.

The AI enriched, delipidated protein precipitate from Example XIV was dissolved in 0.01M Tris-HCl, pH 8.3, buffer made in 6M urea. A 50 μl aliquot was injected in a high-performance liquid chromatography system (HPLC) with a $C_{18}$ column equilibrated in a 20% acetonitrile, 0.1% trifluoroacetic acid (TFA) solution. After injection the sample was eluted with a gradient of acetonitrile from 20 to 70% containing 0.1% TFA at 2 ml/min flow rate. The elution profile, seen in FIG. 14, shows a single major peak. The fractions corresponding to this peak were pooled and acetonitrile was removed by vacuum. The dried pellet was dissolved in phosphate buffer and analyzed by SDS polyacrylamide gel, as in Example VIII. Only a single band, corresponding in molecular weight to about 25,000 daltons, was observed.

The first 39 amino acids of the purified protein was sequenced by conventional methods. Table III below gives the results to the first 8 amino acids of the mature protein. The major sequence, about 95% of the protein, is that of mature apoAI. The minor (5%) sequence corresponds to the proapoAI having six additional N-terminal amino acids.

TABLE III

| | |
|---|---|
| Major Sequence | Asp Glu Pro Pro Gln Ser Pro Trp |
| Minor Sequence | Arg His Phe Trp—Asp Glu Pro Pro Gln Ser Pro Trp |

The sequence shows that the apoAI secreted into the medium is secreted as a processed mature apoAI and not as a pro AI. The first 39 amino acids were sequenced and found to be all correct for mature native apoAI.

EXAMPLE XVI

Nascent HDL-Like Particle Formation with Purified AI

Figure 16:
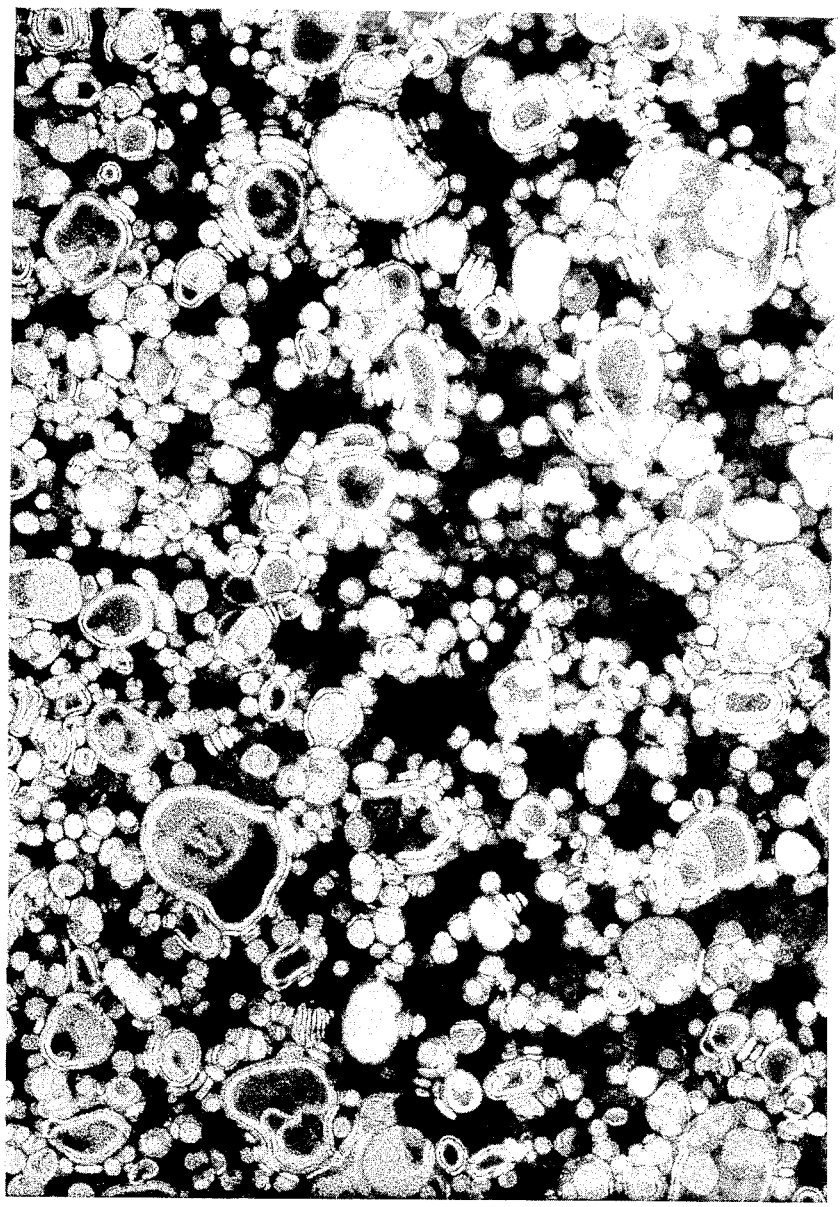
FIG. 16 is a negative-stain electron micrograph of phospholipid vesicles before lipoprotein complex formation by addition of recombinant apoAI.

Repurified egg phosphatidylcholine (PC) obtained from Sigma Chemicals Co. (St. Louis, MO) was dissolved in ethanol (4 mg/ml). The lipid solution (4 ml) was dried under vacuum to a thin film and hydrated with 2 ml of PBS, pH 7.4. The cloudy suspension was sonicated at 15° C. for 1 hour under a stream of nitrogen. The sonicated suspension was centrifuged at 38K rpm for 1 hour, and the supernatant carefully removed. FIG. 16, which is a negative-stain electron micrograph of the liposome preparation shows a mixture of unilamellar and multilamellar structures.

Pure apoAI was incubated with the PC liposomes in a weight ratio of 1:5 at 37° C. for 1 hour. After incubation, apoAI bound to liposomes was separated from free apoAI by gel filtration on 10% Agarose column. This material was then analyzed by negative-stain electron microscopy.

Figure 17:
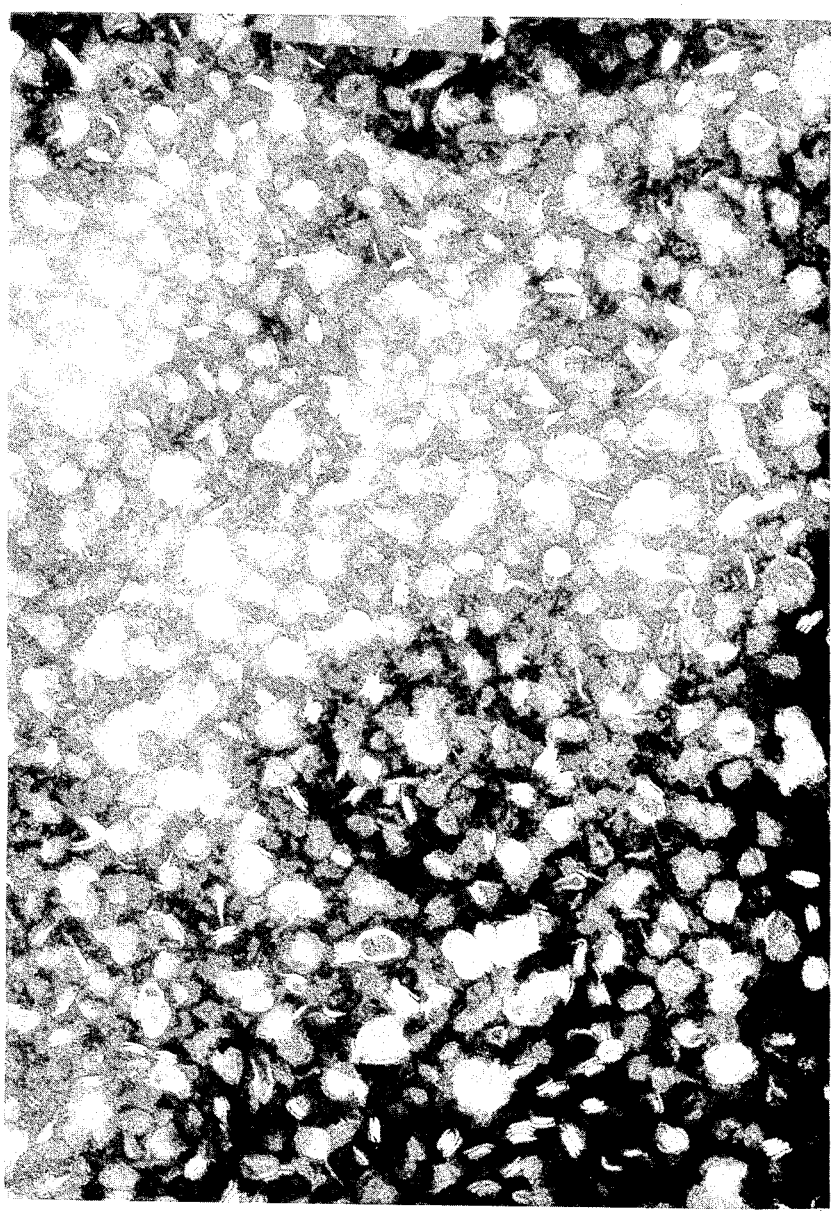
FIG. 17 is a negative-stain electron micrograph of lipoprotein complexes formed by addition of recombinant apoAI to the lipid vesicles of FIG. 16.

FIG. 17 shows (a) the many disc-like structures which have formed in the presence of AI, and (b) the disappearance of more of the clearly identifiable lamellar vesicle structure seen in FIG. 16. The disc-like structures are similar in appearance to nascent HDL-like particles isolated from liver perfusate (see Hamilton, R. L., et al, supra).

EXAMPLE XVII

Stabilized Lipid Emulsion

The emulsion was mixed with purified AI protein from Example XVI, at a wt ratio of 100:2 mg emulsion lipid/mg AI. The mixture was incubated with shaking at 37° C. for 1 hour, to bind apoAI to the emulsion. Unbound apoAI was removed by centrifugation. The stability in serum of the lipid emulsion with and without apoAI was compared. Serum from rats treated with turpentine (5 ml/kg) or from control rats treated the same way but with saline were used. In each test, 180 μl of serum was incubated with 20 μl of lipid emulsion for 2 hours at 37° C. with gentle shaking. After incubation, lipid-particle diameters were determined by laser light scattering using a sub-micron particle analyzer with optional size distribution processor analysis and multiple scattering angle detection (Coulter Model N4, Hialeah, FL).

The results are shown in Table IV below. The lipid emulsion without apoAI was unstable in serum from rats treated with turpentine. The emulsion being characterized by a bimodal distribution of sizes centered around 200 and 500 nm. By contrast, the emulsion containing apoAI showed no significant size change on exposure to serum obtained from turpentine-treated animals. Both emulsions were size stable in serum from control rats.

TABLE IV

| Serum | Emulsion | Size (nm) | % Weight |
|---|---|---|---|
| turp | lipid | 226 ± 64 | 40 |
| | | 588 ± 100 | 60 |
| turp | lipid + apoAI | 329 ± 94 | 100 |
| cont | lipid | 300 ± 67 | 100 |
| cont | lipid + apoAI | 280 ± 40 | 100 |

The results indicate that (a) serum from animals with inflammation contains a factor which promotes fusion of emulsion particles and (b) the fusion event is largely eliminated in emulsion stabilized with apolipoprotein.

EXAMPLE XVIII

Cloning of Receptor Binding and Adjacent Lipid Binding Regions of ApoB

An approximately $5 \times 10^5$ member human adult liver cDNA library (where the insert size averaged 1 kb and the inserts were ligated into the EcoRI site of λgt10) was prepared by the method of Huynh, T., et al, DNA Cloning Techniques: A Practical Approach (1984), Grover, D., ed., IRL Press, Oxford. For screening, $9 \times 10^5$ plaques propagated in C600 (HFL) cells were transferred to replica nitrocellulose filters and processed as described by Seilhamer, J. J., et al, DNA 3:309 (1984). The filters were prewashed for 2 hr in $3 \times$ NaCl/Cit ($1 \times$ NaCl/Cit is 150 mM NaCl/15 mM sodium citrate, pH 7.0), 0.1% SDS at 55° C., and then prehybridized in $6 \times$ NaCl/Cit, 200 μg/ml denatured salmon sperm DNA, $5 \times$ Denhardt's, 0.05% sodium pyrophosphate for 1 hr at 50° C.

A 192-fold degenerate 23 base oligonucleotide probe which encodes, taking account of codon redundancy, the first 8 amino acids of the previously determined sequence of apoB-26 was used as a probe. The probe was 5' end labelled with T4 polynucleotide kinase (PL Biochemicals) and $\gamma$-[$^{32}$P]-ATP, added to the filters and incubated for 14 hr at 50° C. The filters were washed twice at room temperature in $5 \times$ NaCl/Cit, 0.1% SDS, 0.05% sodium pyrophosphate for 15 min and once at 50° C. for 20 min, dried and autoradiographed with intensifying screens.

One positive plaque, designated LB25-1, was purified and the cDNA insert was subcloned in both orientations into M13/mp8 for sequencing. The nucleotide sequence of this 970 bp insert is shown in FIG. 18, along with the deduced amino acid sequence of that reading frame which agrees with the amino terminal sequence determined from the B-26 peptide. The sequence of LB25-1 contains an open reading frame extending 800 nucleotides downstream encoding 294 amino acids, and analysis of the predicted protein sequence directly upstream suggests the presence of a hydrophobic signal sequence preceded by a methionine residue. The EcoRI insert was subcloned into pBR322 to obtain pLB25-1 for amplification. pLB25-1 thus contains some 5' untranslated region, the 28 amino acids of the signal sequence, and the first 266 amino acids of the mature protein.

Additional portions of the apoB encoding sequence were obtained by preparing a $2 \times 10^5$ member human adult intestine cDNA library in λgt10, as described above. The approximately 1 kb insert of pLB25 was denatured and used as probe to isolate a cDNA fragment designated IB7, containing an approximately 1.3 kb insert, about 800 bp of which extended beyond the 3' end of clone pLB25. Isolated, denatured IB7 insert was subcloned into pBR322 for amplification, creating pIB7. The purified pIB7 insert was denatured and used to screen the intestine library. One positive cDNA fragment designated I10 contained an approximately 3 kb insert, about 2.5 kb of which extended beyond the 3' end of IB7. The cDNA insert was subcloned into the EcoRI site of pBR322, creating pB10. Linearized, denatured pB10 insert was used as a probe to obtain a fourth cDNA fragment designated IB-(2)1, containing an approximately 2 kb insert, about 1 kb of which extends beyond the IB-10 sequence. The EcoRI cDNA insert was also subcloned into the EcoRI site of pBR322, creating pB(2)1.

To produce an N-terminal portion of apoB in a suitable host cell, the 4 overlapping clones are digested to produce a single cDNA, as follows. A 479 bp EcoRI-SacI fragment from the pBL25 insert, and a 1162 bp SacI-EcoRI fragment from the pBI7 insert, are ligated into the EcoRI site of pBR322. The resulting plasmid is called pB25-7. When digested with EcoRI and AvaI, the larger fragment contains 1342 bp encoding the signal sequence and first 427 amino acids of apoB.

Two synthetic oligonucleoties, oligo 1 with the sequence 5'-AATTCTGAATGATTGAG-3' and oligo 2 with the sequence 5'-TCGACTCAATCATTCAG-3', are synthesized by standard methods using commercially available reagents, and hybridized by the method of Rossi et al, J Biol Chem 257:9226–9229 (1982). The resulting fragment has the sequence:

oligo 1   5'-AATTCTGAATGATTGAG
oligo 2              GACTTACTAACTCAGCT-5'.

This fragment has an EcoRI overhang, stop codons in all 3 frames, and SalI overhangs. The EcoRI insert, isolated from pBI10, is ligated to the synthetic fragment. The insert now has stop codons and SalI overhangs at both ends. This insert is cloned into the SalI site of pBR322 for amplification, creating p10/stop. When p10/stop is digested with SalI and AvaI, the larger SalI-AvaI fragment contains 2733 bp encoding the carboxy-terminus of the cloned apoB protein portion. The expressed protein terminates (with one extra amino acid due to the insertion of the synthetic fragment) in frame after amino acid 1299.

The amino-terminal EcoRI-AvaI fragment isolated from pB25-7, described above, and the carboxy-terminal AvaI-SalI fragment from p10/stop, also described above, are ligated into EcoRI-SalI digested pBR322. The resulting vector encodes the signal sequence and the first 1299 amino acids of the mature apoB. The amino acid sequence is identical to the first 1299 apoB amino acids shown in FIG. 18 and includes an additional C-terminal aspartic acid residue due to the synthetic fragment. The EcoRI/SalI fragment is then excised and placed in a suitable expression vector, like those described above, for expression of the apoB N-terminal portion.

The coding sequence, or suitable LBP coding portions thereof, can be placed in a suitable expression vector, by techniques like those described above, to achieve apoB expression in the corresponding expression system, such the high-producer CHO cells. The recombinantly produced apoB1 can be purified according to the method of the invention.

Although the invention has been described with respect to specific embodiments and examples, it will be apparent that various changes and modifications can be made without departing from the invention.

It is claimed:

1. A method of producing purified human apoAI comprising:
   providing a Chinese hamster ovary (CHO) cell transformed with an expression vector comprising a regulatable human metallothionein II gene promoter, and an expressible, heterologous gene coding for prepro apoAI, culturing the cell in a serum-free medium under promoter-induction conditions wherein a mixture of extracellular proteins containing mature apoAI is produced,
forming a lipoprotein complex composed of endogenous CHO cell lipid particles and associated apoAI, and
separating the lipoprotein complex from nonlipid-binding proteins in the extracellular medium by floatation.

2. A method of producing human apoAI comprising:
providing a suitable mammalian expression system capable of synthesizing a protein mixture which includes an expressed heterologous gene product wherein the expression system comprises a Chinese hamster ovary (CHO) cell transformed with an expressible, heterologous gene coding for prepro apoAI, and
culturing the CHO cell in a serum-free medium under conditions which permit the production of mature human apoAI protein.

3. The method of claim 2, wherein the gene is introduced in an expression vector under the control therein of a regulatable human metallothionein-II gene promoter.

4. The method of claim 3, wherein the CHO cells include a clonal strain of cells which are selected for high-level expression of the gene.

* * * * *